(12) United States Patent
Sano et al.

(10) Patent No.: US 6,460,592 B1
(45) Date of Patent: Oct. 8, 2002

(54) TUBE CONNECTING APPARATUS

(75) Inventors: Hiroaki Sano, Yamanashi; Narukuni Nakada, Fujinomiya; Akihiko Iguchi, Kasugai; Yoshiyuki Yamada, Kasugai; Masashi Yanagawa, Kasugai; Takeshi Minatani, Kasugai, all of (JP)

(73) Assignee: Tervino Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/557,977

(22) Filed: Apr. 25, 2000

(30) Foreign Application Priority Data

Apr. 27, 1999 (JP) .......................................... 11-120422

(51) Int. Cl.[7] ........................ B32B 31/00; B29C 65/78; A61M 39/00
(52) U.S. Cl. ........................ 156/503; 156/510; 156/556; 156/159; 156/258; 156/304.2; 156/304.6; 156/308.4; 425/108; 277/314; 29/33 T; 604/905
(58) Field of Search ........................ 425/108; 277/314; 29/33 T; 604/905; 156/503, 510, 159, 258, 304.6, 308.4, 556, 304.2; 269/2, 43, 37, 58, 59, 60, 61, 62, 71, 72, 902, 329

(56) References Cited

U.S. PATENT DOCUMENTS

| | | | |
|---|---|---|---|
| 3,695,545 A | 10/1972 | Peters | 242/107.4 |
| 5,802,689 A | 9/1998 | Sano | 29/33 T |
| 6,026,882 A | 2/2000 | Yamada et al. | 156/433 |

FOREIGN PATENT DOCUMENTS

| | | | |
|---|---|---|---|
| EP | 0 778 123 | * | 6/1997 |
| EP | 0 847 847 | | 6/1998 |

* cited by examiner

*Primary Examiner*—Linda Gray
(74) *Attorney, Agent, or Firm*—Oliff & Berridge, PLC

(57) ABSTRACT

A tube connecting apparatus is arranged to hold tubes in a first tube holder and a second tube holder, to rotate a pair of rotatable clamping members which include separable pieces disposed in rotational symmetry for holding the tubes in either or both of the first tube holder and the second tube holder, to heat and melt the tubes by a heated cutting plate moving therebetween to cut the tubes, and to weld cut end faces of the different tubes. When the pair of clamping members are in a state of not holding the tubes rotation preventing members fixedly lock the clamping members in a predetermined position, preventing the clamping member from being rotated.

13 Claims, 19 Drawing Sheets

TUBE CONNECTING APPARATUS

BACKGROUND OF THE INVENTION

1. Field of the Invention

The present invention relates to a tube connecting apparatus for melting to cut flexible tubes and for connecting the tubes by mutually contacting the cut end faces.

2. Description of the Related Art

A tube connecting apparatus is used, for instance, for transferring a dialysis solution to an abdominal cavity of a patient who requires Continuous Ambulatory Peritoneal Dialysis (CAPD) by providing connection between a transfer tube connected with the abdominal cavity and a tube connected with a dialysis pack.

An example for connecting operations of a tube connecting apparatus will be briefly explained below. As exemplarily shown in FIG. 18, two tubes 7, 8 are grasped at two portions, that is, between a fixed clamp 311 and a movable clamp 312 of a first tube holder 301 and between a fixed clamp 313 and a movable clamp 314 of a second tube holder 302. The movable clamps 312, 314 are moved into contact with, and away from, the fixed clamps 311, 313. The tubes 7, 8 grasped by the first tube holder 301 and the second tube holder 302 are squeezed flat in cross section, closing the interior of the tubes.

Then, a heated cutting plate (hereinafter referred to as a "wafer") 6 is moved upwards between the first tube holder 301 and the second tube holder 302, thereby melting to vertically cut the tubes 7, 8.

In the first tube holder 301 is provided a pair of semicircular rotor pieces 303, 304 which are brought into contact with each other to form a clamp rotor 305.

After the cutting of the tubes 7, 8, the rotation of the clamp rotor 305 grasping the cut tubes (7a, 8a) of one side of the tubes (7, 8), as shown in FIG. 19, inverts the cut tubes 7a, 8a while allowing their cut end faces to slide along a side surface of the wafer 6.

Upon completion of inversion of the cut tubes 7a, 8a, the wafer 6 is retracted when the cut end faces of mutually different tubes (7a and 8b, 8a and 7b) are positioned coaxially, facing each other, and the cut end faces of the different tubes are pressed to each other to be welded. Thus, two tubes 9, 10 are formed as illustrated in FIG. 20.

The above described tube connecting apparatus is arranged such that inversion of the cut tubes is performed by the clamp rotor 305 comprising the pair of rotor pieces 303, 304. FIG. 21 is a sectional view of the clamp rotor 305 mounted in the first tube holder 301.

The clamp rotor 305 includes of the pair of semicircular rotor pieces 303, 304 with teeth formed on the periphery thereof, and is so constituted as to make one gear when the rotor pieces 303, 304 come into contact with each other. At a center of the clamp rotor 305, that is, at the center of the contact surfaces of the rotor pieces 303, 304, U-shaped grooves 331, 332 are formed deep enough to allow the insertion of one tube, and closing portions 333, 334 are provided forming shallow grooves to squeeze and grasp the tubes.

The rotor pieces 303, 304 are respectively mounted in rotor mounting portions 323, 324 formed in blocks 321, 322 constituting the fixed clamp 311 and the movable clamp 312.

On the other hand, a drive gear 306 which is in mesh with the rotor piece 303(304) is rotatably mounted in a gear mounting portion 325 formed continuously to the rotor mounting portion 323. The drive gear 306 is further connected to a motor shaft of a driving motor (not illustrated).

When the tubes 7, 8 are grasped and then cut as shown in FIG. 18, the unillustrated driving motor is driven at a specified timing such that rotation is transmitted to the driving gear 306. In this manner, the clamp rotor 305 is rotated within the first tube holder 301 and the rotor pieces 303, 304 are turned to change the placement of cut tubes 7a, 8a.

However, the conventional tube connecting apparatus mentioned above has the following disadvantages.

(1) The first and second holders 301, 302 need to be moved closer to each other for securing operations of pressing the cut end faces of the tubes to each other after retracting the wafer 6. Therefore, for clamping the tubes 7, 8 by the first tube holder 301 and the second tube holder 302, the movable clamp 312 is fixed to the fixed clamp 311 and, separately therefrom, the movable clamp 314 is fixed to the fixed clamp 313. In this way, in order to fix the movable clamps 312, 314 to the fixed clamps 311, 313, similar works need to be repeated, of manually or automatically, thereby causing useless redundancy in view of operation as well as structural arrangement.

(2) The conventional tube connecting apparatus employing the clamp rotor 305 is arranged such that the rotor pieces 303, 304 are exposed to the exterior when the blocks 321, 322 are separated. In case the user presses the rotor pieces 303, 304, therefore, the rotor pieces 303, 304 will be displaced from each position after tube connection where the tubes are held symmetrically with respect to each other.

Thus, in case the rotor pieces 303, 304 should be brought into contact with each other while still displaced, either one will be pushed by the other to be slightly rotated. Thus the clamp rotor 305 will be misaligned relative to a reference condition in which the rotor pieces 303, 304 are accurately mounted in symmetric relation to each other in the blocks 321, 322 as shown in FIG. 21. Accordingly, if the apparatus is actuated in this condition with the tubes 7, 8 being not clamped symmetrically, misalignment of the cut end faces of the tubes 7, 8 is caused by inversion of the clamp rotor 305, which may result in connection errors.

(3) While the tubes 7, 8 are clamped by the first and second tube holders 301, 302, if the movable clamps 312, 314 are erroneously separated from the fixed clamps 311, 313 before the tubes 9, 10 are formed, i.e., before the tubes 7, 8 are alternately joined to each other, the tubes 7, 8 will be released from the first and second holders 301, 302. As a result, the alternate joining of the tubes 7, 8 can not be ensured. It is therefore necessary to prevent the fixed clamps 311, 313 from being separated from the movable clamps 312, 314 before completion of alternate connection of the tubes. However, the conventional apparatus is provided with no functions for reliable of such an event prevention.

SUMMARY OF THE INVENTION

The present invention has been made in view of the above circumstances and has an object to overcome the above problems and to provide a tube connecting apparatus capable of reliably connecting tubes.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a tube connecting apparatus including: a first tube holder provided with a pair of holding members for holding a plurality of flexible tubes; a second tube holder provided with a pair of holding members for holding the plurality of flexible tubes, one or both of the first tube holder and the second tube holder including a pair of rotatable clamping members for holding the tubes, the clamping members including separable pieces disposed in rotational symmetry; cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and rotation preventing means for preventing rotation of the clamping members being in predetermined positions in the respective holding members while the pair of clamping members are in a state of not holding the plurality of flexible tubes.

In the above tube connecting apparatus, while the clamping members are not in a clamping position with respect to the tubes, the rotation preventing means functions to prevent the rotation of the clamping members to lock them in position within the respective holding members. Thus, the connection of tubes can be reliably ensured.

In the above tube connecting apparatus, preferably, the rotation preventing means is constructed of an engaging groove formed in the clamping member and a protrusion provided in a resilient member having an urging force toward the clamping member, the protrusion being insertable into the groove of the clamping member by the urging force of the resilient member, and the protrusion is retracted from the groove of the clamping member against the urging force of the resilient member by a pressing member that presses the resilient member away from the clamping member when the pair of clamping members hold the tubes.

In the above tube connecting apparatus, preferably, the resilient member is a flat spring and is integrally formed with the protrusion insertable into the groove of the clamping member.

Preferably, the groove of the clamping member is formed in the clamping member in a correspondent position with the protrusion.

Preferably, the rotation preventing means is constructed of an engaging groove formed in the clamping member, an engaging slider formed with an engaging portion insertable into the groove of the clamping member, and a linkage mechanism for sliding the engaging slider forward and backward in synchronization with the pair of holding members operated to hold and release the tubes.

Preferably, the linkage mechanism of the rotation preventing means includes a lever axially supported so as to be able to oscillate, the lever being oscillated by an external force applied thereto when the pair of holding members hold the tubes, thereby retracting the engaging slider urged to the clamping member against the urging force.

Preferably, the groove of the clamping member is formed in the clamping member in a correspondent position with the engaging portion.

According to another aspect of the invention, there is provided a tube connecting apparatus including: a first tube holder provided with a pair of holding members for holding a plurality of flexible tubes; a second tube holder provided with a pair of holding members for holding the plurality of flexible tubes, one or both of the first tube holder and the second tube holder including a pair of rotatable clamping members for holding the tubes, the clamping members including separable pieces disposed in rotational symmetry; cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; wherein at least either one of the holding members of at least either one of the first tube holder and the second tube holder is provided with a positioning hole and the other one with a positioning protrusion engageable with the positioning hole, and positioning of the pair of holding members set together is performed by engaging the protrusion with the positioning hole.

In the above tube connecting apparatus, with the positioning hole and the positioning protrusion, the pair of holding members of the first tube holder and/or the second tube holder can be set in position with respect to each other, which makes it possible to reliably grasp the tubes and squeeze them flat. Accordingly, the interiors of the tubes squeezed can be tightly closed to prevent liquid leakage therefrom when the tubes are cut.

According to another aspect of the present invention, there is provided a tube connecting apparatus including: a first tube holder provided with a pair of holding members for holding a plurality of flexible tubes, a second tube holder provided with a pair of holding members for holding the plurality of flexible tubes; cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and supporting means provided in at least either one of the first tube holder and the second tube holder for supporting the tubes one over another.

Accordingly, at least one of the first and second tube holders is provided with the supporting means for supporting the tubes therein, so that the tubes can be reliably held one over another in the holding members, preventing connection errors.

In the tube connecting apparatus, preferably, the supporting means is provided with a pair of supporting claws projecting for pinching the tubes therebetween, each of the supporting claws being formed with a protrusion for preventing the tubes from coming off.

According to another aspect of the present invention, there is provided a tube connecting apparatus including: a first tube holder provided with a pair of holding members for holding a plurality of flexible tubes; a second tube holder provided with a pair of holding members for holding the plurality of flexible tubes; cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and detecting means for detecting presence or absence of the tubes in at least one of the first tube holder and the second tube holder.

The tube connecting apparatus provided with the detecting means which detects the presence/absence of the tubes can avoid the connection errors caused by clamping errors with respect to the tubes.

In the above tube connecting apparatus, preferably, the detecting means includes a plunger which protrudes in response to urging force of urging members and a sensor for detecting a position of the plunger, and the plunger is retracted by an elastic force of the held tubes against the urging force of the urging members and a position of the retracted plunger is detected by the sensor.

Preferably, the plunger is provided in either or both of the tube holders and a surface from which the plunger projects is flat.

Preferably, the pair of holding members is formed with a groove for holding the tubes, the groove being formed with closing members for flattening and closing the held tubes at one end thereof, the plunger is disposed within the groove, and a closing position at which the closing members close the tubes is closer to the plunger side than a center of the tubes.

According to another aspect of the present invention, there is provided a tube connecting apparatus including: a first tube holder provided with a pair of holding members for holding a plurality of flexible tubes; a second tube holder provided with a pair of holding members for holding the plurality of flexible tubes, one or both of the first tube holder and the second tube holder including a pair of rotatable clamping members for holding the tubes, the clamping members including separable pieces disposed in rotational symmetry; cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and supporting means for arranging the tubes one over another in an outside of at least either one of the first tube holder and the second tube holder; wherein the supporting means includes a pair of claws for pinching the tubes therebetween, the claws being urged in directions of moving toward each other by urging members and being movable away from each other in association with rotation of the tubes against the urging force of the urging members while the tubes are rotated as held by the clamping member.

Since the above tube connecting apparatus is provided with the supporting means constructed of a pair of claws for pinching the tubes therebetween with the aid of the urging members which urge the claws in directions of moving toward each other, the claws being movable away from each other against the urging force in correspondence with the rotation of the tubes, the tubes can be reliably held one over another. Specifically, the tubes when disposed one on top of the other can be surely supported in position, while the tubes can be smoothly inverted due to mutual outward sliding of the claws.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
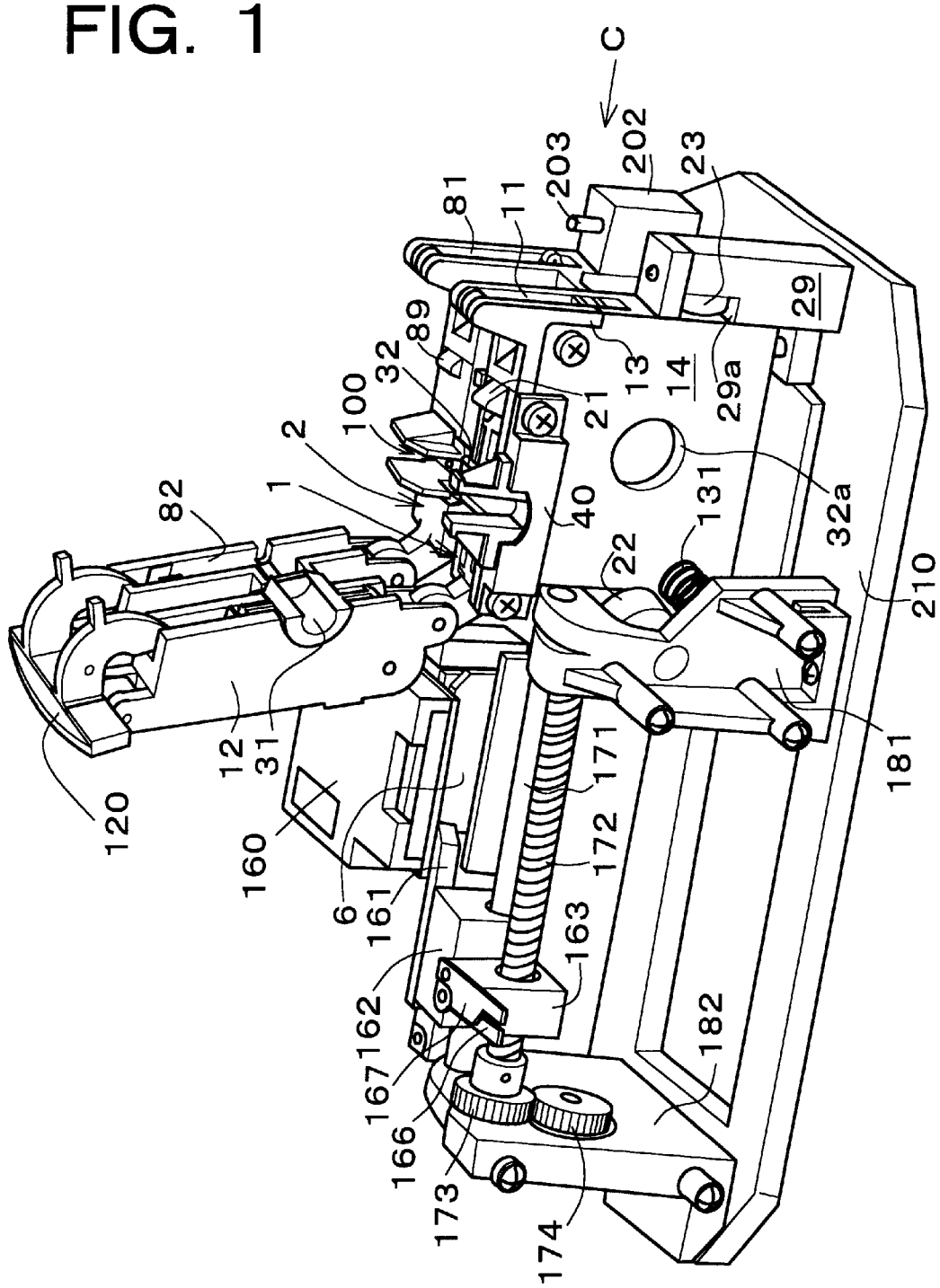
FIG. 1 is a perspective view of an internal structure of a tube connecting apparatus in an embodiment according to the present invention.
Figure 2:
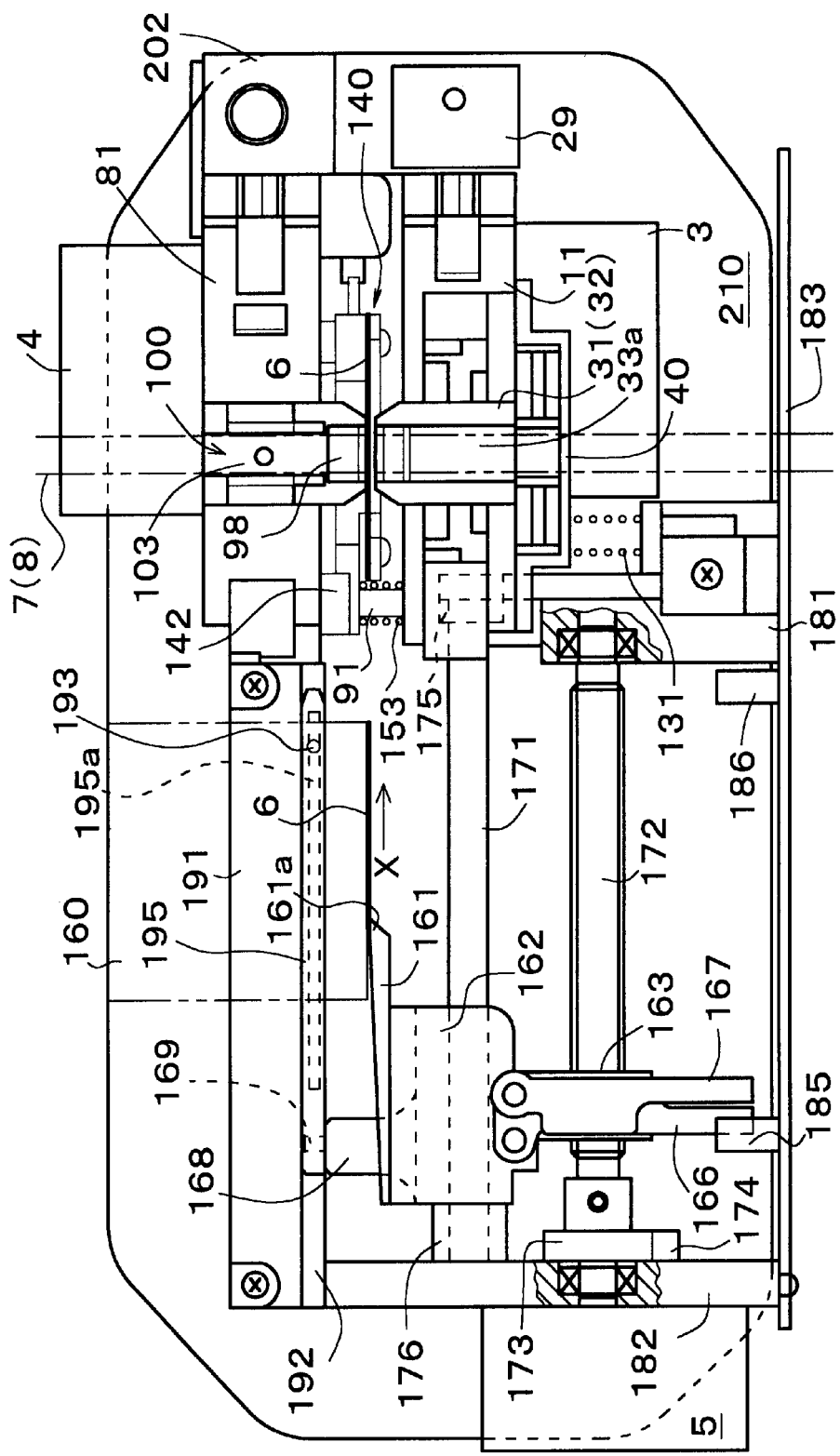
FIG. 2 is a plan view of the tube connecting apparatus in the embodiment.

A detailed description of a preferred embodiment of a tube connecting apparatus embodying the present invention will now be given referring to the accompanying drawings. FIG. 1 is a perspective view of an internal arrangement of the tube connecting apparatus in the present embodiment. FIG. 2 is a plan view thereof (while movable clamps 12, 82 are omitted).

The tube connecting apparatus includes a tube holding mechanism for holding tubes, a cutting mechanism for moving a cutting plate, or a wafer 6, with respect to the tubes, and a wafer transferring mechanism for transferring a new wafer 6 for each tube connecting operation. The arrangement of the tube holding mechanism will be first explained.

The tube holding mechanism is for holding and grasping two tubes 7, 8 set one on top of the other at two positions, vertically inverting cut tubes of one side of the tubes after cutting, and pressing the cut end faces of the inverted tubes to those of the other cut tubes to connect the cut ends of different tubes. The tube holding mechanism is mainly constructed of a first tube holder 1 and a second tube holder 2. The first tube holder 1 is provided with a fixed clamp 11 and a movable clamp 12 which is connected to the fixed clamp 11 by a pin joint. Similarly, the second tube holder 2 is provided with a fixed clamp 81 and a movable clamp 82 connected to the fixed clamp 81 by a pin joint. It is to be noted that the fixed clamps 11, 81 and the movable clamps 12, 82 correspond to the holding members of the invention.

The first tube holder 1 and the second tube holder 2 are disposed in parallel with each other at a specific distance. The second tube holder 2 is fixed on a base 210 while the first tube holder 1 is slidably arranged to adjust the distance between itself and the second tube holder 2. Between the first and second holders 1, 2 is disposed a wafer holder 140 constituting the cutting mechanism for moving a wafer 6 in an orthogonal direction with respect to the tubes 7, 8 held in the first and second tube holders 1, 2.

Figure 3:
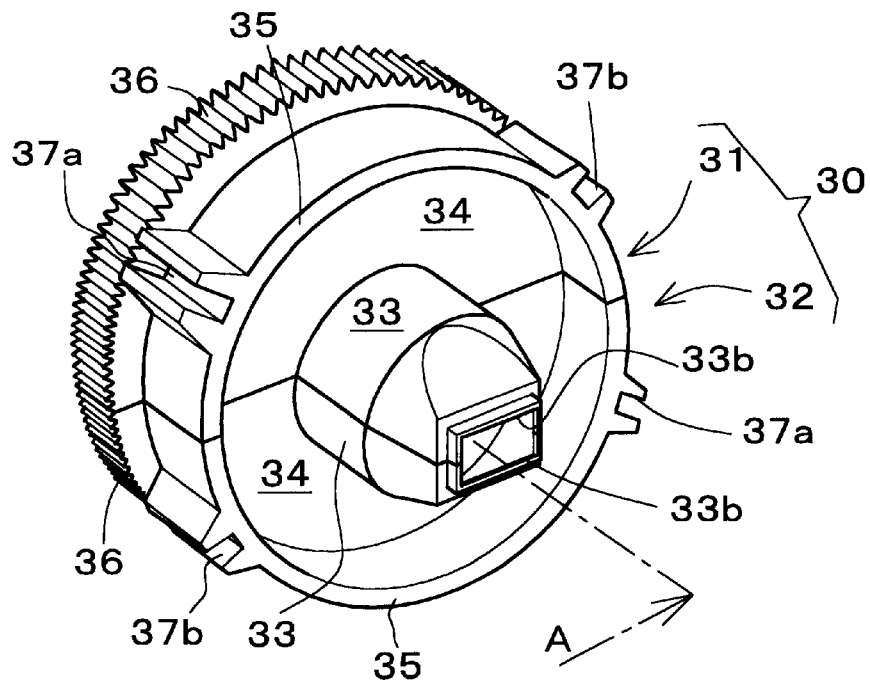
FIG. 3 is a perspective view of a clamp rotor of the tube connecting apparatus in the embodiment.
Figure 4:
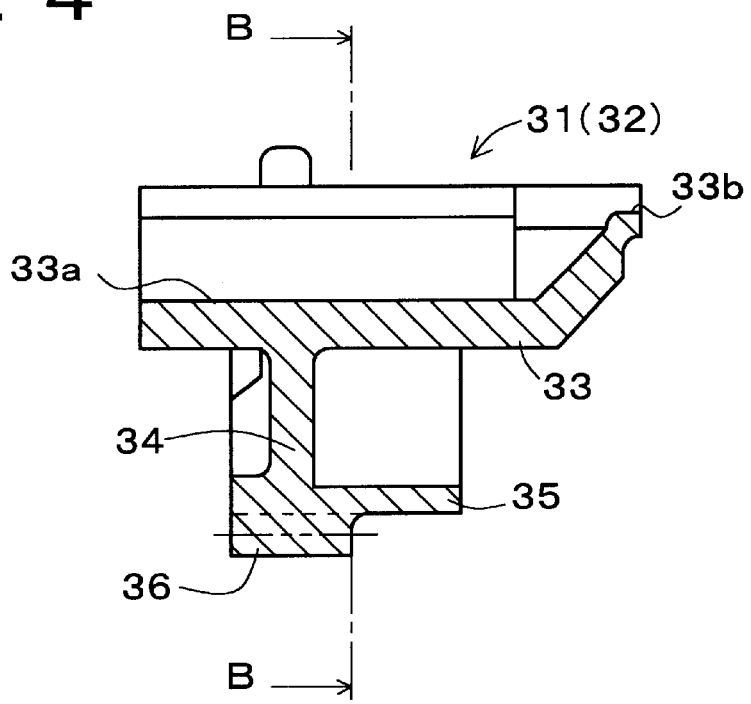
FIG. 4 is a sectional view of a rotor piece viewed from the direction indicated by an arrow A in FIG. 3.

A clamp rotor 30 for inverting the tubes cut with the wafer 6 is provided in the first tube holder 1. FIG. 3 is a perspective view showing the clamp rotor 30. FIG. 4 is a sectional view of a rotor piece 31(32) of the clamp rotor 30 viewed from the direction indicated by an arrow A in FIG. 3. It should be noted that the rotor pieces 31, 32 correspond to the clamping members of the invention.

The clamp rotor 30 is constructed of a pair of rotor pieces 31, 32 which are of semicircular shapes in rotational symmetry as if a gear is divided into halves. Thus, each of the rotor pieces 31, 32 is of a similar semicircular shape. When the half-divided surfaces of the rotor pieces 31, 32 are brought into contact with each other, one clamp rotor 30 is formed. More particularly, the clamp rotor 30 is constructed of centrally located tube holding portions 33, 33 for holding the tubes, flange portions 34, 34 protruding outward in a radial direction from the tube holding portions 33, 33, rim portions 35, 35 formed perpendicularly at outer peripheries of the flange portions 34, 34. On the rim portions 35 are formed rotor gears 36, 36 as well as two pairs of locking grooves 37a, 37b.

The tube holding portions 33, 33 are constructed of holding grooves 33a, 33a and closing portions 33b, 33b formed by tapering a cylindrical portion toward the center axis to provide a tip end portion with a narrower width. Each of the holding grooves 33a, 33a is of a substantially semicircular section having a depth corresponding to approximately the outside diameter of the tube 7(8). The closing portions 33b, 33b are arranged in mutually symmetrical relation to provide sufficient clearance to squeeze the two tubes set one on top of the other therein into flat shapes, thereby to firmly close the interior of the tubes.

The locking grooves 37a, 37a and the other locking grooves 37b, 37b are formed on the rim portions 35, 35 in identical positions of the rotor pieces 31, 32. This is for corresponding the locking grooves 37a, 37a to a locking mechanism of the fixed clamp 11 and for corresponding the locking grooves 37b, 37b to a locking mechanism of the movable clamp 12. This locking mechanism will be mentioned later. Each of the locking grooves 37a, 37b has a predetermined width defined by two protruding walls formed on the rim portion 35.

The fixed clamp 11 and the movable clamp 12 of the first tube holder 1 in which the rotor pieces 31, 32 are mounted will next be explained.

Figure 5:
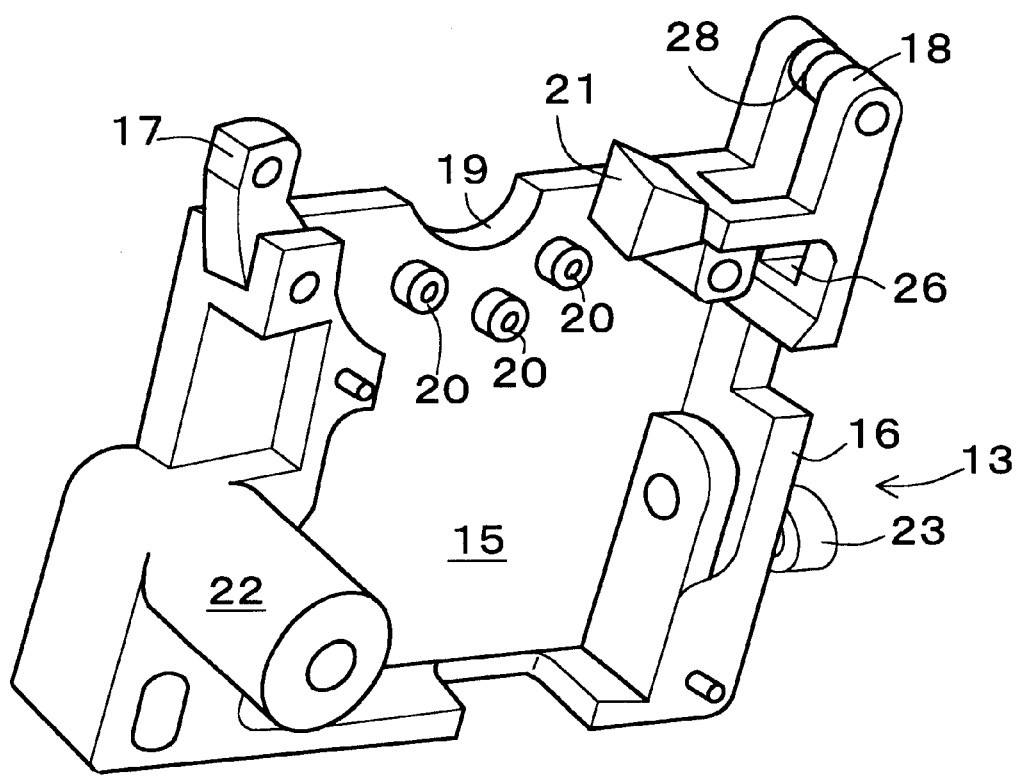
FIG. 5 is a perspective view of a fixed clamp body of the tube connecting apparatus in the embodiment.

The fixed clamp 11 is constructed of a fixed clamp body 13 shown in FIG. 5 and a body cover 14 (see FIG. 1) secured to the body 13. The fixed clamp body 13 has an outer frame 16 formed protruding on a lateral wall 15 as illustrated, and the body cover 14 is screwed to this outer frame 16. The fixed clamp 11 is thus of a hollow shape which is open in the upper surface, in which the above-described rotor piece 31(32) is mounted. A stepping motor 3 (see FIG. 2) is further attached to the body cover 14. In association therewith, a row of gears is provided within the fixed clamp 11 for transmitting rotational output of the stepping motor 3 to the rotor piece 31(32).

The fixed clamp body 13 is formed with a single supporting bracket 17 and a forked supporting bracket 18 at both upper corner portions thereof as shown in FIG. 5. The single supporting bracket 17 is provided for a pin-joint with the movable clamp 12. A bearing 28 is pivotally mounted between the forked supporting bracket 18.

A rotation supporting groove 19 that is a semicircular cutout for supporting the tube holding potion 33 of the rotor piece 31(32) is formed at an upper side of the lateral wall 15 of the fixed clamp body 13 and an upper side of the body cover 14 (not shown). Rollers 20 for rotationally supporting the rotor piece 31(32) are pivotally mounted on the lateral wall 15 on a concentric circle with the rotation supporting groove 19. The three rollers 20 are arranged such that two side rollers 20 are symmetrically disposed with respect to a central roller 20 at intervals of 60°.

A positioning projection 21 is provided to the fixed clamp body 13 as to protrude from the upper side of the lateral wall 15.

Figure 6:
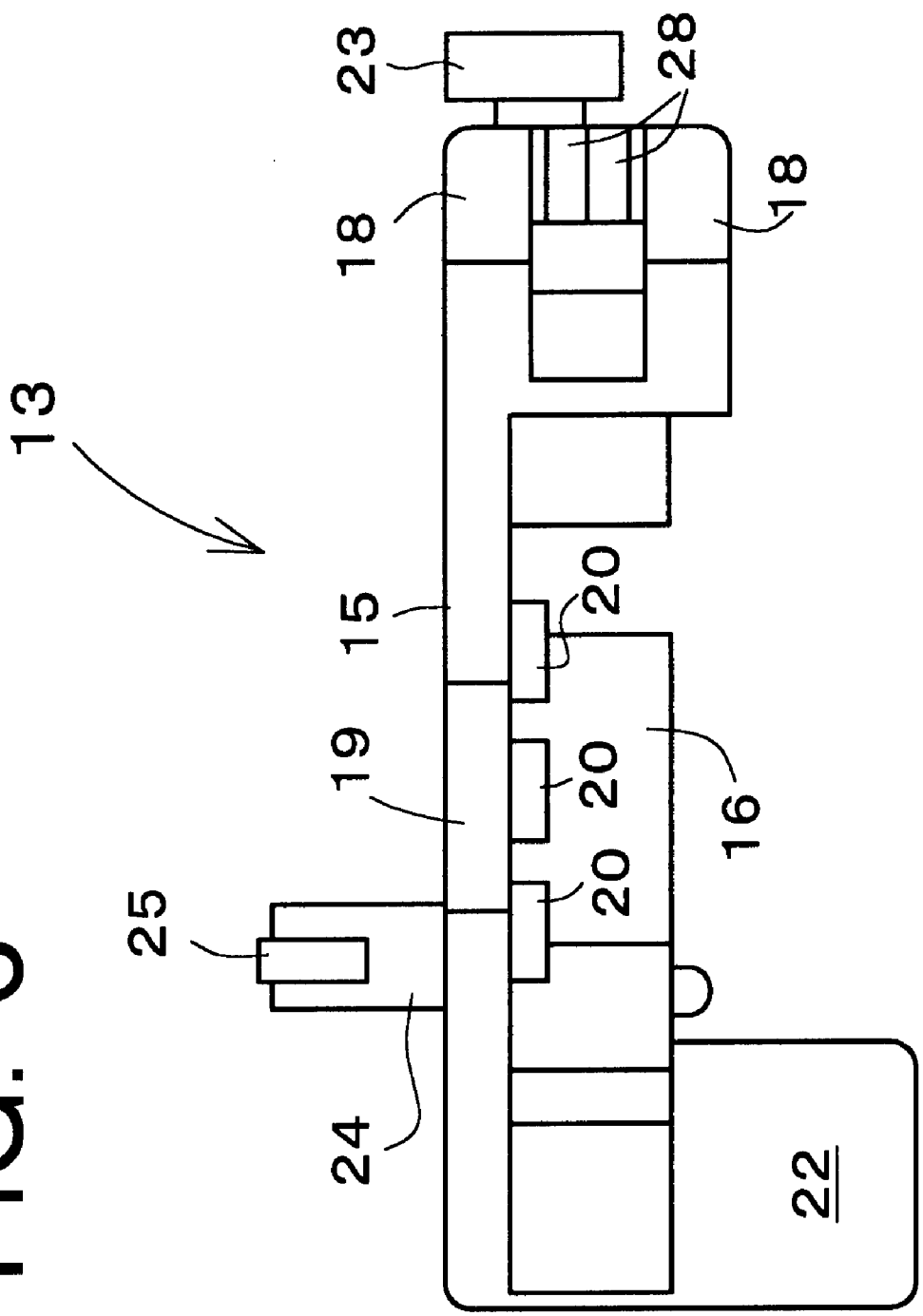
FIG. 6 is a plan view of the fixed clamp body shown in FIG. 5.

The fixed clamp body 13 is, as mentioned above, configured such that the first tube holder 1 is disposed parallel to and movable with respect to the second tube holder 2. FIG. 6 is a plan view of the fixed clamp body 13.

The fixed clamp body 13 is provided with a slide tube 22 formed on the lateral wall 15 as to protrude perpendicularly thereto and a guide roller 23 supported rotatably in a direction along an axis of the slide tube 22. The slide tube 22 is fitted on a protruding guide rod provided in the second tube holder 2, which will be mentioned later. The guide roller 23 is disposed within a guide groove 29a of a guide block 29 fixed to the base 210 as shown in FIG. 1.

In this manner, the fixed clamp 11 of the first tube holder 1 is attached such that the fixed clamp body 13 is supported above and in out-of-contact with the base 210 by the slide tube 22 and the guide roller 23.

The fixed clamp body 13 is further provided with a pressing arm 24 formed protruding toward the second tube holder 2 side as shown in FIG. 6. At the tip end of the arm 24, a roller bearing 25 is pivotally supported.

The fixed clamp 11, movably supported with the slide tube 22 and the guide roller 23, is always urged to the second tube holder 2 side by a spring 131 arranged between the fixed clamp 11 and a supporting wall 181 fixed onto the base 210 as shown in FIG. 1.

Thus, the roller bearing 25 provided at the tip end of the pressing arm 24 is always brought into contact with a driving cam within the second tube holder 2 (described later) so that the bearing 25 rolls along a cam surface of the driving cam.

Figure 7:
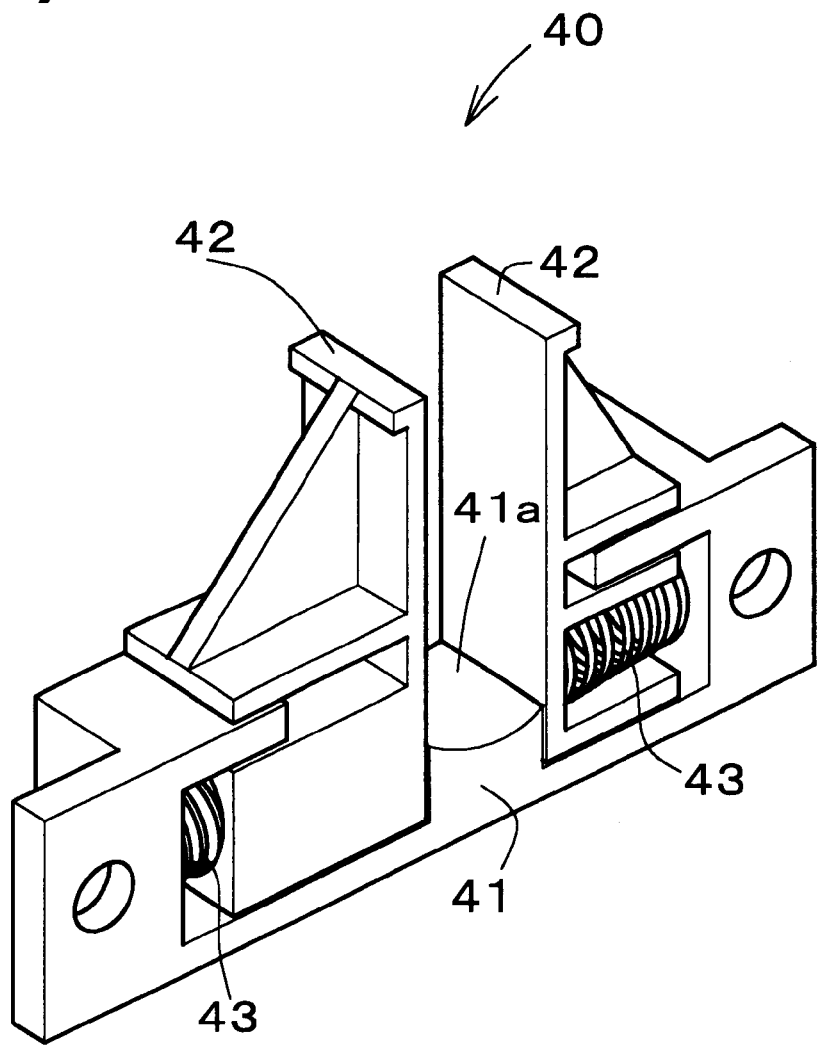
FIG. 7 is a perspective view of a tube guide of the tube connecting apparatus in the embodiment, showing a mounting surface side with respect to a body cover.

A tube guide 40 (see FIG. 1) for accurately setting the tubes is fixed to the body cover 14 of the fixed clamp 11. FIG. 7 is a perspective view of the tube guide 40 showing the side which is in contact with the body cover 14.

The tube guide 40 is constructed of a guide body 41, a pair of guide claws 42, 42, and springs 43, 43 disposed respectively outside of the claws 42, 42 so as to urge them inwards (toward each other).

Specifically, a warped groove 41a is formed in the center of the guide body 41 on which the tubes are set. The guide claws 42, 42, attached to the guide body 41 and arranged on both sides of the groove 41a, are urged to the groove 41a side by the springs 43, 43. The guide claws 42, 42 are thus urged in directions of moving toward each other. These guide claws 42, 42 are movable in the urging directions. It should be noted that the pair of guide claws 42, 42 are identical in configuration and disposed such that one faces the front while the other one is reversed, whereby they may be used on either side, thus enabling the use of common parts.

Figure 8:
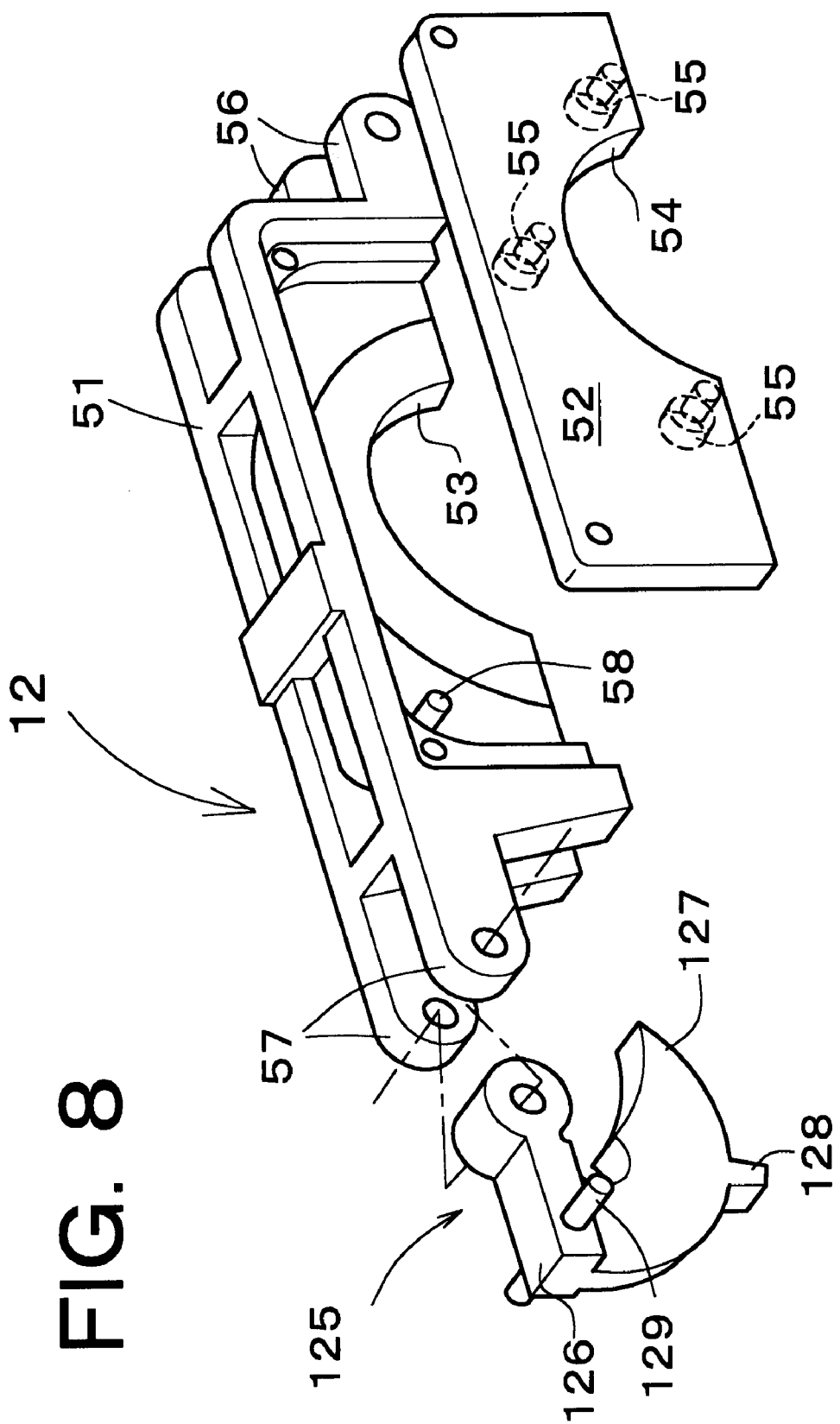
FIG. 8 is a perspective exploded view of a movable clamp of a first tube holder of the tube connecting apparatus in the embodiment.

Next, FIG. 8 is a perspective exploded view of the movable clamp 12 of the first tube holder 1 seen from the second tube holder 2 side. The movable clamp 12 is constructed of a movable clamp body 51 and a body cover 52 attached to the body 51, thus becoming hollow, similarly to the fixing clamp 11, and the rotor piece 31(32) is mounted therein.

Rotationally supporting grooves 53 and 54 that are semicircular cutouts are formed at corresponding positions of the movable clamp body 51 and the body cover 52. Rollers 55 for rotationally supporting the rotor piece 31(32) are pivotally mounted on the body cover 52 on a concentric circle with the rotationally supporting groove 54. The three rollers 55 are arranged such that two side rollers 55, 55 are symmetrically disposed with respect to a central roller 55 at intervals of 60°. Furthermore, forked supporting brackets 56, 57 for pin joints are provided protruding at both ends of the movable clamp body 51.

Figure 9:
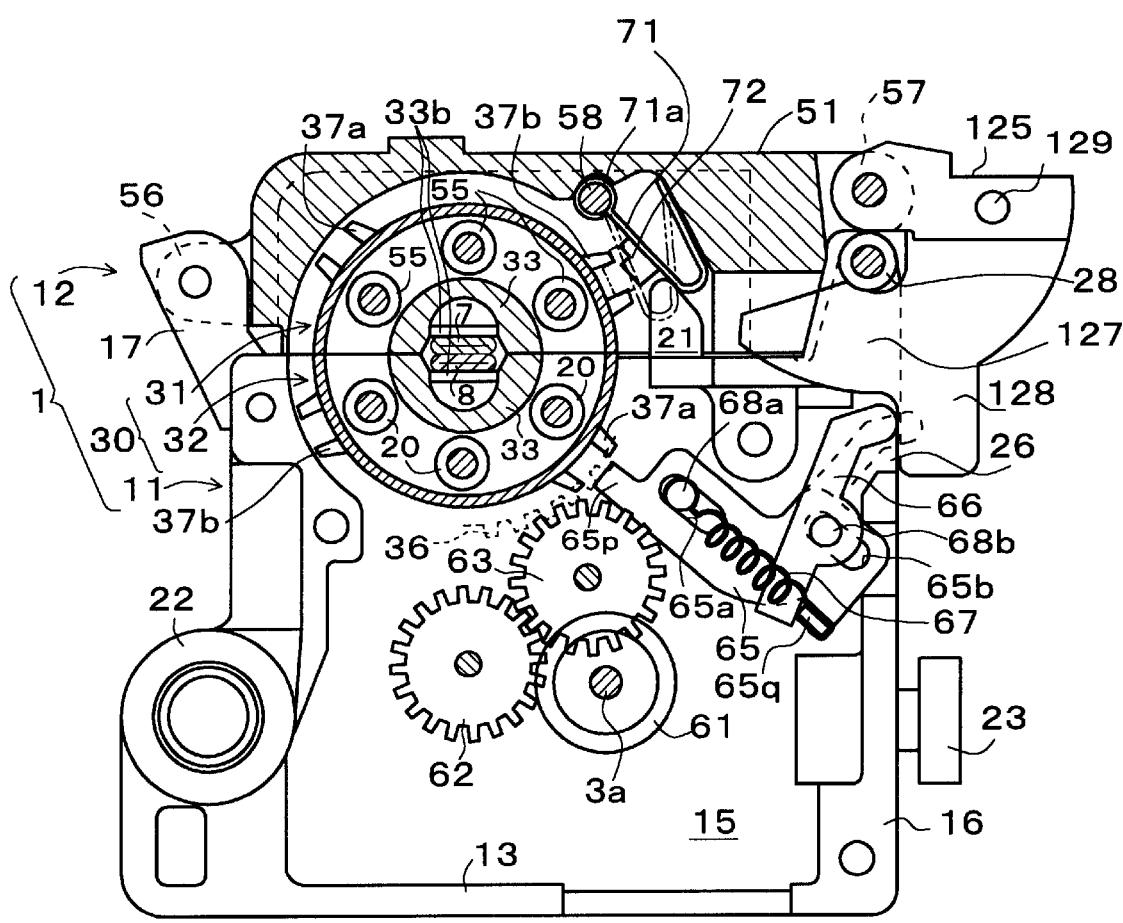
FIG. 9 is a sectional view of the first tube holder in the embodiment.

Next, FIG. 9 is a sectional view of the first tube holder 1. More particularly, this is a schematic view showing the fixed clamp 11 with the fixed clamp body 13 from which the body cover 14 is removed and the movable clamp 12 with the clamp body 51 illustrated in section.

The first tube holder 1 is assembled by pin-joining the fixed clamp 11 to the movable clamp 12 by the respective supporting brackets 17, 56. The movable clamp 12 thus can be oscillated or turned about the pin joining the brackets 17 and 56 so that an oscillation end of the body 51 moves into contact with the fixed clamp 11 (a closed position of the movable clamp 12) or away from the fixed clamp 11 (an open position) as illustrated in FIG. 1. A buckle 125 (see FIG. 8) is pin-joined to the supporting bracket 57 formed at the oscillation end of the body 51 of the movable clamp 12. The buckle 125 is configured such that a jaw portion 127 may be hooked over the bearing 28 of the fixed clamp 11 and be locked in the state shown in FIG. 9.

In the clamping condition of the first tube holder 1 shown in FIG. 9, the set tubes 7, 8 (see FIG. 2) are held one over the other in the holding grooves 33a, 33a of the rotor pieces 31, 32 so that they are symmetrically clamped and closed by the closing portions 33b, 33b as illustrated. It is to be noted that the clamp rotor 30 in FIG. 9 is illustrated in a section along the line B-B of the rotor pieces 31, 32 shown in FIG. 4.

The rotor pieces 31, 32 are mounted in the movable clamp 12 and the fixed clamp 11 respectively so that the three rollers 55 and the three rollers 20 are inserted between the tube holding portions 33 and the rim portions 35. In the clamping condition as illustrated, the rotor pieces 31, 32 form one clamp rotor 30 (see FIG. 3), and the rollers 20, 55 are located at equal intervals (intervals of 60°) on a concentric circle. The clamp rotor 30 is placed with the closing portions 33b, 33b protruding to the second tube holder 2 side.

The fixed clamp 11 is configured such that the stepping motor 3 (see FIG. 2) is fixed to the body cover 14, a driving gear 61 is attached to a motor shaft 3a of the motor 3, the shaft 3a being inserted through a through hole 32a (see FIG. 1) into the interior of the fixed clamp 11. The driving gear 61 is in mesh with an access gear 62 and a drive gear 63, and the driving gear 63, in turn, is in mesh with the rotor gear 36 of the clamp rotor 30.

The fixed clamp 11 and the movable clamp 12 are provided with locking mechanisms, serving as rotation preventing means, for supporting the rotor pieces 31 and 32 in position within the corresponding clamps 11 and 12 in order to prevent displacement of the rotor pieces 31 and 32 from the positions shown in FIG. 9 while no tube is set or the tubes set therein are not clamped. Each of the locking mechanisms is arranged to fit into the locking groove 37a or 37b provided in the rotor pieces 31, 32 for limiting displacement, or misalignment, of the rotor pieces 31, 32.

The locking mechanism on the fixed clamp 11 side will first be explained. This locking mechanism is constructed of a slide plate 65 which is an engaging slider, a crank plate 66, and a spring 67 as illustrated in FIG. 9. In the slide plate 65 are formed two circular slide holes 65a, 65b extending lengthwise of the plate and located in parallel with each other. The slide plate 65 is slidably supported by engaging the holes 65a, 65b with pins 68a, 68b formed projecting on the lateral wall 15 of the fixed clamp body 13.

The slide plate 65 is formed with an engaging portion 65p at a tip end thereof, protruding in a longitudinal direction of the slide holes 65a, 65b, and a hook portion 65q at the other end thereof, bent almost perpendicularly from the plate surface. The slide plate 65 is always urged toward the center of the clamp rotor 30 by a spring 67 anchored at one end to the pin 68a and at the other end to the hook portion 65q.

On the other hand, the crank plate 66 serving as a lever is rotatably supported at substantially a central portion thereof about the pin 68b so that one end (lower end) having a straight linear shape is brought into contact with an abutment surface of the hook portion 65q of the slide plate 65, the surface being inside in an urging direction, while the other end (upper end) having an L-shaped configuration is disposed to be insertable in a window portion 26 formed in the fixed clamp body 13.

The locking mechanism on the movable clamp 12 side is constructed of a flat spring 71 having a U-shaped configuration and an engaging piece 72 fixed on the spring 71. This flat spring 71 is a resilient member of the invention. The engaging piece 72 has an engaging protrusion insertable in the locking groove 37 of the clamp rotor 30. The flat spring 71 is formed, at one end, with a supporting ring 71a which is anchored to a pin 58 formed projecting from an inside wall of the movable clamp body 51. The other end of the flat spring 71 is abutted against an inside wall of the movable clamp body 51 so that the inside wall receives the urging force of the flat spring 71. At this time, the engaging piece 72 is urged toward the center of the clamp rotor 30 by the flat spring 71.

The locking grooves 37a, 37b respectively formed in the rotor pieces 31, 32 are arranged to face the engaging portion 65p and the engaging piece 72 in a clamping condition as indicated in FIG. 9, thereby uniquely positioning the rotor pieces 31, 32. Each of the locking grooves 37a, 37b is defined by inner opposite parallel surfaces of the two protruding walls. In association therewith, the engaging portion 65p and the engaging piece 72 which are inserted into those grooves are formed in a square protruding shape corresponding to the groove shape.

Figure 10:
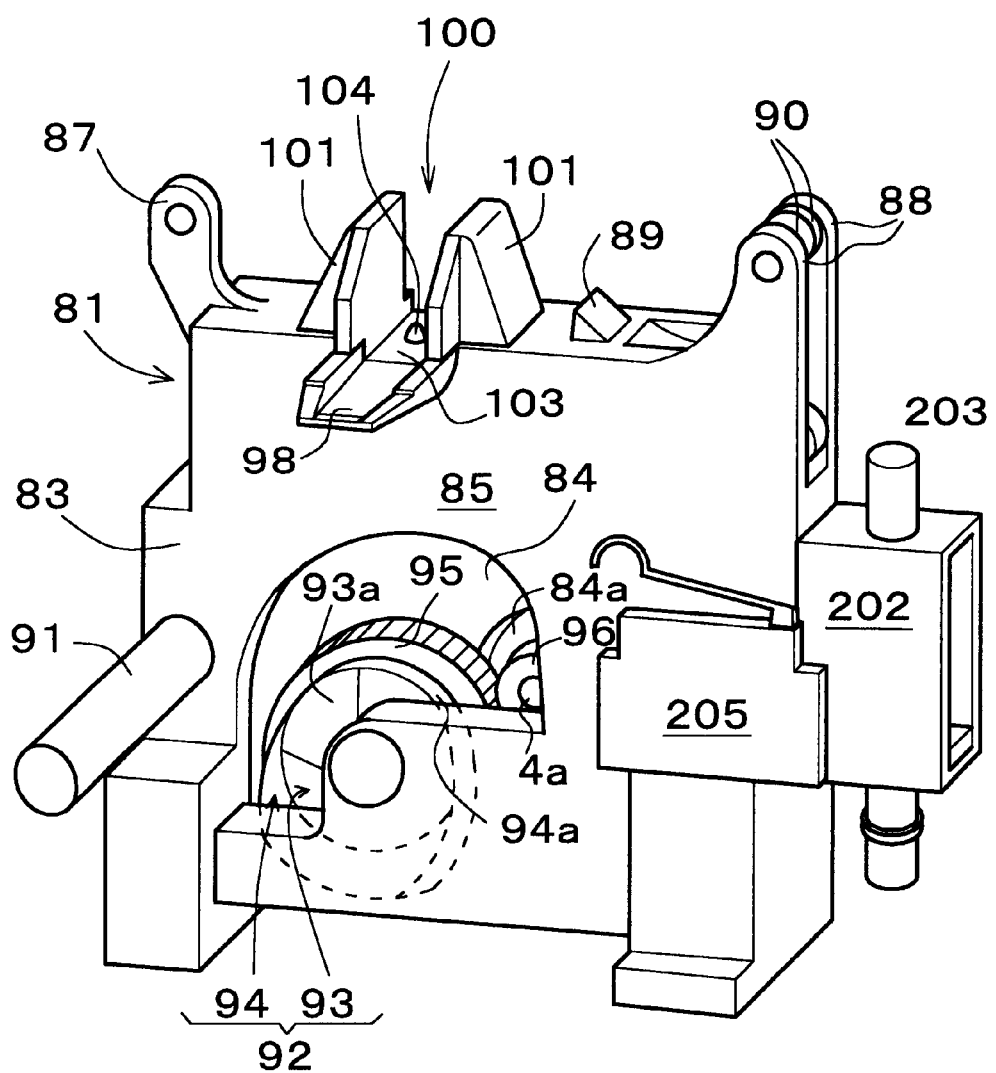
FIG. 10 is an external perspective view of a fixed clamp of a second tube holder in the embodiment.
Figure 11:
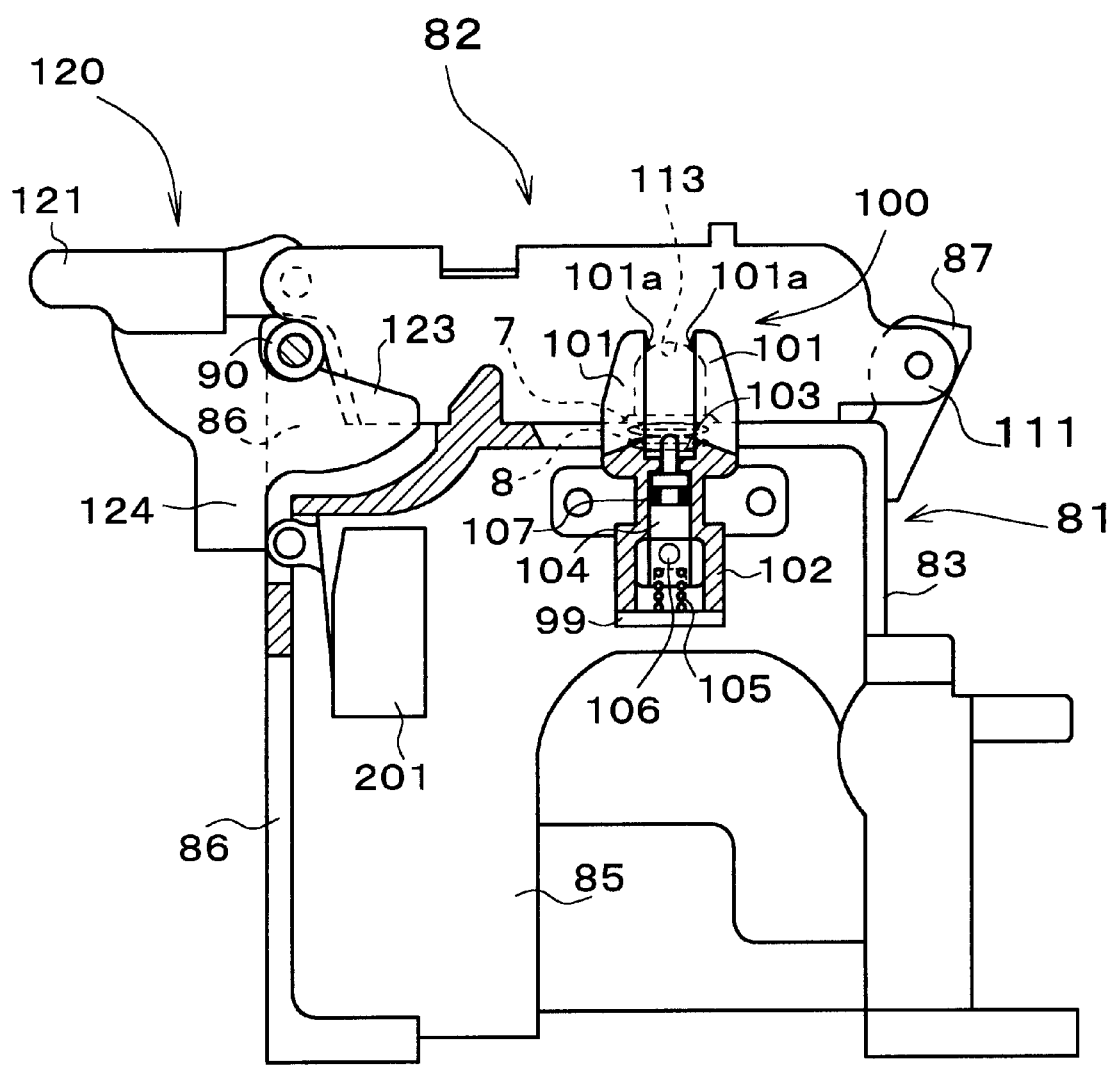
FIG. 11 is a side view of the fixed clamp body of the second tube holder in the embodiment.

The second tube holder 2 will be next explained in detail. FIG. 10 is an external perspective view of a fixing clamp 81 of the second tube holder 2 viewed from the first tube holder 1 side. FIG. 11 is a perspective view showing a fixed clamp body of the second tube holder 2.

This fixed clamp 81 is constructed of a hollow fixed clamp body 83, similar to the first tube holder 1, and a body cover 84 covering the hollow body 83 from the exterior. This body 83 is configured such that an outer frame 86 as illustrated is perpendicularly provided to a lateral wall 85 and the body cover 84 is fixed to this outer frame 86 by screws.

The fixed clamp body 83 is formed with a single supporting bracket 87 and a forked supporting bracket 88, respectively, at both upper corner portions thereof. The single supporting bracket 87 is provided for a pin joint with the movable clamp 82, while a bearing 90 is pivotally supported between the forked supporting bracket 88. A positioning protrusion 89 is formed in the fixed clamp body 83 to protrude upward from an upper side of the lateral wall 85 as shown in FIG. 10.

The fixed clamp body 83 is, as shown in FIG. 10, provided with a guide rod 91 formed perpendicular to the lateral wall 85 for supporting the slide tube 22 (see FIG. 5) of the first tube holder 1. The lateral wall 85 is largely cutout for exposing an internally provided driving cam 92 to the exterior.

The driving cam 92 is formed integrally with a reduction gear 95 and is pivotally mounted within the fixed clamp body 83 in the illustrated position. The driving cam 92 is constituted of a circular shaped slide cam 93 and an eccentric shaped cutting cam 94 that are integrally formed. The slide cam 93 is formed, on the end face, with a slide cam surface 93a with a slope for changing a height of the cam 93 in the axial direction. The cutting cam 94 is formed, on the outer periphery, with an eccentric cam surface 94a.

On the other hand, the stepping motor 4 (see FIG. 2) is fixed to the body cover 84, as shown in FIG. 10. A driving gear 96 is attached to a motor shaft 4a of the motor 4, the shaft 4a being inserted into the interior of the body 83 through a through hole 84a. The driving gear 96 is in mesh with the reduction gear 95.

A tube guide 100 is provided in the fixed clamp body 83 as shown in FIG. 11. The tube guide 100 is constructed of a pair of guide claws 101, 101 serving as supporting means for supporting tubes set therein. These guide claws 101, 101 are disposed penetrating the outer frame 86 forming an upper surface of the body 83 to protrude upward. These guide claws 101 are integrally formed with a plunger case 102 disposed inside the fixed clamp body 83.

Projections 101a, 101a are formed in the guide claws 101, 101 at respective tip end portions, projecting inwards, for preventing the tubes set in the guide 100 from coming off. A holding groove 103 provided between the guide claws 101, 101 is continuous to and flush with a holding groove 98 formed in the fixed clamp body 83. On the other hand, the plunger case 102 is a housing in which a stepped plunger 104 is disposed slidably in a vertical direction. The housing is open in the bottom and fixedly mounted on a supporting plate 99 formed protruding inwards from the lateral wall 85 in the fixed clamp body 83.

The plunger 104 is urged upward by a spring 105 arranged between the plunger 104 and the supporting plate 99 so that a tip end of the plunger 104 penetrates to protrude from a bottom surface of the holding groove 103 of the tube guide 100. The plunger 104 is also provided with a magnet 106 embedded in a lowermost step portion thereof such that a position of this magnet 106, that is, the height of the plunger 104 may be detected by a tube holding detecting sensor (not shown) fixed in the body cover 84. The presence or absence of a tube within the holding groove 103 is determined upon detection of the height of the plunger 104.

An O-ring 107 is fitted to the plunger 104 for preventing dialysis liquid from flowing into the plunger case 102 in case the liquid leaking from cut tubes should enter the through hole formed in the bottom surface of the holding groove 103.

Figure 12:
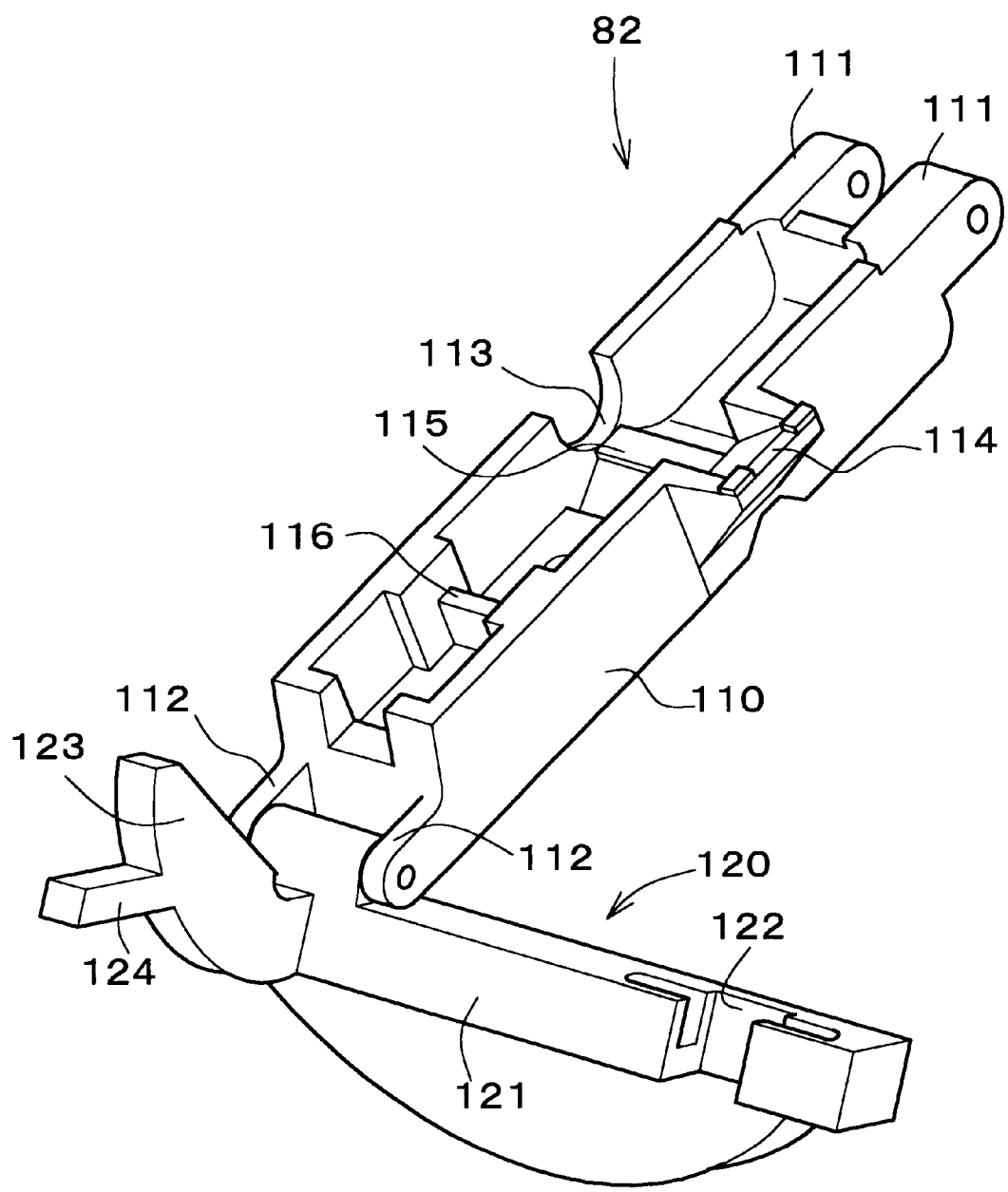
FIG. 12 is a perspective view of the movable clamp and a buckle in the embodiment.

FIG. 12 is a perspective view showing a fixed clamp 82 and a buckle 120. The movable clamp 82 is constructed of an integrally-molded hollow clamp body 110 both ends of which are formed with forked supporting brackets 111, 112. This clamp body 10 is provided with a U-shaped groove 113 for passing a tube through, a closing portion 114 formed protruding in a lateral direction, a pressing portion 115 between the groove 113 and the closing portion 114. The pressing portion 115 is protruded as to slightly press the tube. The movable clamp body 110 is further formed with an engaging wall 116 which is disposed closer to an oscillation end side of the body 110 (the buckle 120 side) and will be brought into contact with the positioning protrusion 89 of the fixed clamp body 83.

The buckle 120 is pin-joined to the supporting bracket 112 of the movable clamp body 110. The buckle 120 is of a configuration which can be integrally assembled with the buckle 125 of the first tube holder 1 shown in FIG. 8. Specifically, a grasping plate 121 of the buckle 120 is largely projecting to one side (the first tune holding holder 1 side) at which a groove 122 is formed for allowing an inserting portion 126 and a pin 129 of the buckle 125 to be inserted therein. Furthermore, the buckle 120 is formed with a jaw portion 123 and a pressing protruding piece 124, similarly to the buckle 125, at a position corresponding to the supporting bracket 112.

As illustrated in FIG. 11, the second tube holder 2 is assembled by pin-joining the movable clamp 82 to the fixed clamp body 83 by the supporting brackets 87, 111. The movable clamp 82 can be oscillated or turned about the pin joining the brackets 87, 111 so that an oscillation end (the buckle 120 side) moves into contact with the fixed clamp 81 (a closed position of the movable clamp 82) or away from the fixed clamp 81 (an open position) as shown in FIG. 11.

On the other hand, the jaw 123 of the buckle 120 pin-joined to the oscillation end of the body 110 of the movable clamp 82 is hooked over a bearing 90 and is locked in a clamping condition as illustrated in FIG. 11.

In the clamping condition of the second tube holder 2 shown in FIG. 11, the holding groove 98 of the fixed clamp body 83 and the closing portion 114 of the movable clamp body 110 are arranged to have a clearance therebetween sufficient to squeeze the tubes 7,8 set therein one over the other into flat shapes, thereby to close the interior of the tubes.

The first tube holder 1 and the second tube holder 2, constructed as above, are disposed on the base 210 in parallel with each other, as shown in FIGS. 1 and 2. More particularly, the fixed clamp body 83 of the second tube holder 2 is directly fixed onto the base 210 and the slide tube 22 of the first tube holder 1 is slid on the guide rod 91 formed in the fixed clamp body 83 of the second tube holder 2 (see FIG. 10). At this time, both the fixed clamps 11, 81 are parallel to each other. Since the other end of the fixed clamp 11 (opposite to the slide tube 22 side) is also supported by the guide roller 23, the first tube holder 1 is enabled to move to adjust a distance between itself and the second tube holder 2 while maintaining a parallel relation to the second tube holder 2 and to the base 210.

In the first tube holder 1, movably supported in parallel relation to the second tube holder 2 as mentioned above, the fixed clamp body 13 is always urged toward the second tube holder 2 side by the spring 131. With this arrangement, the roller bearing 25 of the pressing arm 24 protruding from the first tube holder 1 (see FIG. 6) is brought into contact with the slide cam 93 of the driving cam 92 provided in the second tube holder 2. The roller bearing 25 is allowed to always roll along the cam surface of the slide cam 93.

Figure 13:
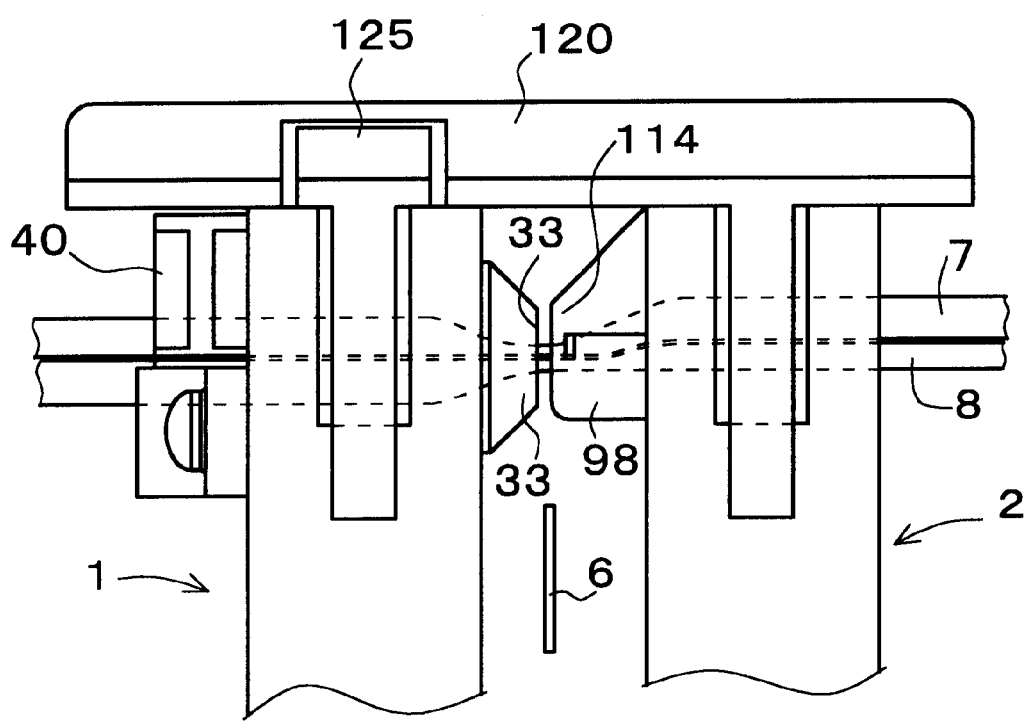
FIG. 13 is a front view of the first and second tube holders viewed from the direction indicated by an arrow C in FIG. 1.

As shown in FIG. 13, the first tube holder 1 and the second tube holder 2 are arranged to have a slight space between two closing portions, that is, the position of the holding grooves 33a, 33a of the rotor piece 31(32) and the position the closing portion 114 of the movable clamp 82 at the tip end of the holding groove 98 of the fixed clamp 81. FIG. 13 is a front view of the first tube holder 1 and the second tube holder 2 viewed from the direction indicated by an arrow C in FIG. 1.

Here, the holding groove 98 of the fixed clamp body 83 has a bottom surface flush with a height of the closing portion 33b of the rotor piece 31(32) located on a lower side so as to correspond with the height of the tubes 7, 8 grasped and closed by the clamping rotor 30.

Therefore, the tubes 7, 8 are squeezed symmetrically with respect to an intermediate point of respective center axes of the tubes 7, 8 (i.e., a contact line of both tubes 7, 8) in the clamp rotor 30 side, while the tubes 7, 8 are squeezed to the bottom surface side of the holding groove 98 in the fixed clamp body 83 side as shown in FIG. 13.

A cutting mechanism is further provided between the first tube holder 1 and the second tube holder 2 for vertically moving the wafer 6 for cutting the tubes 7, 8 squeezed and held in the holders 1, 2.

Figure 14:
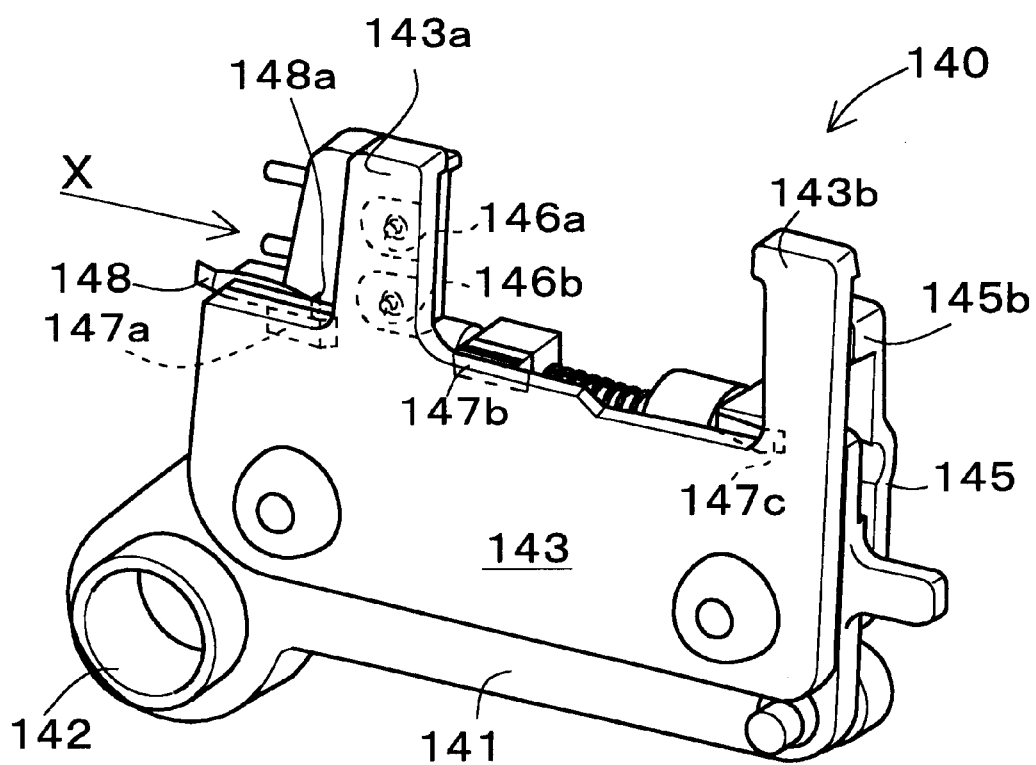
FIG. 14 is a perspective view of a wafer holder viewed from the first tube holder side in the embodiment.
Figure 15:
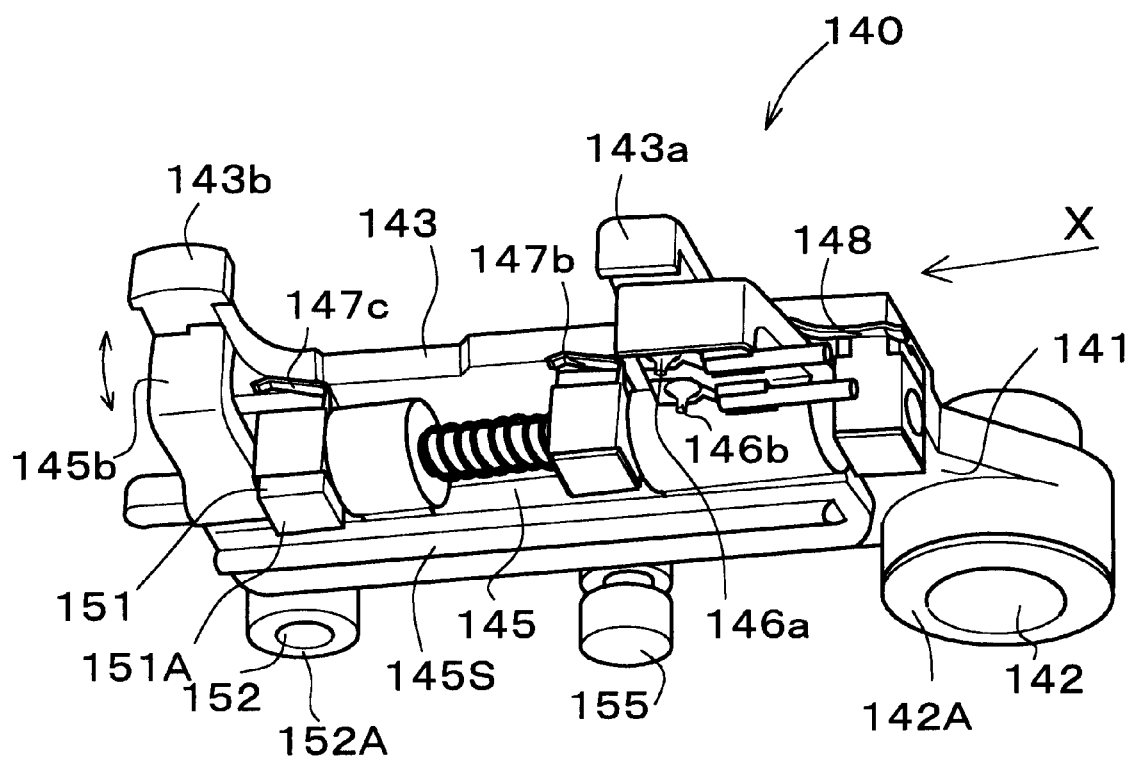
FIG. 15 is a perspective view the wafer holder viewed from the second tube holder side in the embodiment.

This cutting mechanism will be explained below. A wafer holder 140 for holding and vertically moving the wafer 6 is disposed between the above-described first and second tube holders 1 and 2. FIGS. 14 and 15 are perspective views showing the wafer holder 140 for holding the wafer 6. More particularly, FIG. 14 is a view of the holder 140 seen from the first tube holder 1 side and FIG. 15 a view of the same seen from the second tube holder 2 side.

The wafer holder 140 is supported so as to be able to oscillate or rotate about the guide rod 91 of the second tube holder 2, and is constructed of a base plate 141 provided with an oscillation tube 142 which is slid onto the guide rod 91, a fixed plate 143 and an opening/closing plate 145 which are provided on both sides of the base plate 141. The fixed plate 143 is fixed to the base plate 141 on the first tube holder 1 side, and a groove (not shown) is formed between the plates to allow the wafer 6 to pass through. The fixed plate 143 is provided with two stop portions 143a, 143b extending upward with turned ends for preventing an upward displacement of the wafer 6.

The opening/closing plate 145 is supported rotatably about a shaft provided at a lower portion with respect to the base plate 141. When a lower portion of the opening/closing plate 145 below the shaft-supported portion is urged by an urging member, the plate 145 is rotated to move an upper portion away from the fixed plate 143, or to an open position. Upon release of the urging force the plate 145 is rotated to move the upper portion into contact with the fixed plate 143, or to a closed position. On the opening/closing plate 145 are arranged electrodes 146a, 146b at a position corresponding to the stop portions 143a of the fixed plate 143. When the electrodes 146a, 146a come into contact with a resistor terminal of the wafer 6 loaded in the wafer holder 140, electricity is supplied to the resistor through the electrodes 146a, 146a. A pressing piece 145b is formed in the opening/closing plate 145 as to face the stop portion 143b of the fixing plate 143. A single linear projection 1455 is further formed in an outer surface of the opening/closing plate 145 in parallel to a transferring direction of the wafer 6.

To the base plate 141 are provided positioning flat springs 147a, 147b, 147c for positioning the wafer 6 by pressing the same against the fixing plate 143, and a retraction-preventing flat spring 148 disposed in overlapping relation to the rearmost flat spring 147a. The positioning flat springs 147a, 147b, 147c are disposed so as to press the wafer 6 at three points transversely aligned in almost the center of the height of the wafer 6 loaded in the wafer holder 140. The retraction-preventing flat spring 148 is formed with a turned end 148a for interrupting a retraction path of the wafer 6 that has already passed the spring 148.

For appropriately performing cutting and connecting of tubes, the wafer 6 is required to move in an orthogonal direction to tubes 7, 8 held in the first tube holder 1 and the second tube holder 2. For that purpose, the wafer holder 140 needs to be oscillated along an orthogonal surface without deflecting or wobbling. In the present embodiment, the lateral wall 85 of the fixed clamp body 83 directly fixed to the base 210 (see FIG. 10) is used as a reference surface so that the wafer holder 140 is slid along the reference surface to be oscillated.

In the wafer holder 140, an end surface 142A of the oscillation tube 142, an end surface 151A of an attaching block 151 to which the positioning flat spring 147c is attached, and an end surface 152A of a sliding tube 152 fixed at a tip end of the base plate 141 are arranged flush with each other.

The wafer holder 140 is then fitted on the guide rod 91 of the second tube holder 2 together with the first tube holder 1 and is urged to the second tube holder 2 side by a spring 153 disposed on the holder 140 and the first tube holder 1 (see FIG. 2). With this arrangement, each of the end surfaces 142A, 151A, 152A of the wafer holder 140 are continuously pressed against the lateral wall 85 of the fixed clamp body 83 serving as a reference surface. In this state, the wafer 6 loaded in the wafer holder 140 is orthogonal with respect to the tubes 7, 8.

The wafer holder 140 is also provided with a roller bearing 155 that is pivotally mounted on a shaft fixed to the base plate 141 on the surfaces 142A, 151A, 152A side. Though not shown in the drawings, the wafer holder 140 is attached in a state where the roller bearing 155 is inserted in the fixed clamp body 83 (see FIG. 10) and is put on a peak portion of the eccentric cam surface 94a of the cutting cam 94 of the driving cam 92.

The wafer transferring mechanism for transferring the wafer 6 into the wafer holder 140 will next be explained. A plurality of the wafers 6 are accommodated in a stacked state in a wafer cassette 160 as shown in FIGS. 1 and 2. Of those accommodated wafers, a wafer 6 is pushed out onto a transferring line and is transferred in a direction as indicated by the arrow X by means of a transfer top 161 which moves along the transferring line (see FIG. 2).

The transfer top 161 is formed, at a tip end, with a stepped claw portion 161a corresponding to the thickness of the wafer 6. The transfer top 161 is integrally formed with a slider 162. This slider 162 is slidably supported on a guide rod 171 fixed to between supporting walls 181, 182 fixed on the base 210.

Furthermore, a male screw 172 is fixed to between the supporting walls 181 and 182 in parallel with the guide rod 171. A female screw holding balls (namely, a ball thread arrangement) is provided in a female screw block 163 integrally formed with the slider 162. This female screw is engaged with the male screw 172 to constitute a ball screw.

A transmission gear 173 is fixed to the male screw 172 at an end on the supporting wall 182 side. A stepping motor 5 is fixed to the supporting wall 182 from outside with a motor shaft going inward through the supporting wall 182. A driving gear 174 is fixed to the motor shaft of the stepping motor 5 and is engaged with the transmission gear 173.

Markers 166, 167 which are two plates partially overlapped one over the other are attached on an upper surface of the female screw block 163. On the other hand, a control substrate 183 is fixed to the supporting walls 181, 182 as illustrated in FIG. 2. The control substrate 183 is provided with a standby-detecting sensor 185 and a transfer-detecting sensor 186. The standby-detecting sensor 185 is a sensor for detecting a standby position of the transfer top 161 based on the position of the marker 166. The transfer-detecting sensor 186 is a sensor for detecting a transferring position of the transfer top 161 based on the position of the marker 167. The markers 166, 167 are pivotally supported on the female screw block 163 such that an opening degree between tip ends of the markers 166, 167, serving as an object to be detected, may be adjusted.

Stoppers 175, 176 for preventing overrun of the slider 162 are fitted on the guide rod 171 and in contact with the supporting walls 181, 182, respectively.

The slider 162 is also provided with a supporting arm 168 extending from below the transfer top 161 and a pin 169 protruding from a tip end of the supporting arm 168. A prism-shaped beam 191 is fixed between the supporting wall 182 and the fixed clamp block 81 of the second tube holder 2 and in parallel with the guide rod 171. The beam 191 is formed with a stepped corner constituting a rail 192. A prism-shaped operating rod 195 is placed on the rail 192. A guide groove 195a is formed in a rear surface of the operating rod 195 (i.e., a surface which is in contact with the rail 192) along a longitudinal direction thereof. A protruding guide pin 193 formed in the rail 192 is inserted in the groove 195a.

The tip end of the supporting arm 168 formed extending from the slider 162 is brought into contact with a side surface of a rear end portion of the operating rod 195, and the pin 169 provided at the tip end of the supporting arm 168 is loosely received in a bore formed in the operating rod 195.

Tube connecting operations of the tube connecting apparatus of the above-described arrangement will be explained below. The tube connecting apparatus is entirely covered by a cover (not shown) such that upper portions of the fixed clamps 11, 81 and the movable clamps 12, 82 are exposed to the exterior. Therefore, by opening the movable clamps 12, 82 upward as illustrated in FIG. 1, the upper surfaces of the fixed clamps 11, 81 will appear to enable setting of tubes 7, 8. Thus, a user sets two tubes 7, 8 (see FIG. 2) one over the other in the tube guides 40, 100. At this time, the tubes 7, 8 are placed with their central axes being parallel one over the other. This is because the distance between the guide claws 42, 42 of the tube guide 40 (see FIG. 7) and that between the guide claws 101, 101 of the tube guide 100 (see FIG. 11) are adjusted to the outer diameter of the tube 7(8).

The tubes 7, 8 once set in the tube guide 100 are prevented from coming off the holding groove 103 by the protrusions 110a, 101a of the guide claws 101, 101. The tubes thus press down the plunger 104 protruding through the bottom surface of the holding groove 103 owing to their elastic force (see FIG. 11).

When the plunger 104 is pushed downward by the tubes against the urging force of the spring 105, the movement of the magnet 106 is detected by the sensor (not shown) and a corresponding signal is transmitted to a controller of the apparatus.

After setting the tubes 7, 8, the user closes the movable clamps 12, 82 of the tube connecting apparatus in the condition shown in FIG. 1 by grasping the buckle 120. Thus, the movable clamps 12, 82 are set on the fixed clamps 11, 81 to clamp the tubes 7, 8 held one on top of the other.

The buckle 120 being integrally assembled with the buckle 125 as described above, the user can simultaneously close both the movable clamps 12, 82 through operation by holding the grasping plate 121 (see FIG. 12). Then, when the buckle 120 with the movable clamps 12, 82 being set on the fixed clamps 11, 81 (see FIGS. 9 and 11) is rotated, the jaw portions 123, 127 are hooked over the bearings 28, 90 of the fixed clamps 11, 81 into a locking state.

In association with operations of setting the tubes 7, 8 and locking through the buckle 120 by the user, the tube connecting apparatus performs tube set confirmation and lock releasing of the clamp rotor 30.

When the user first locks the buckles 120, 125, the pressing protruding piece 124 of the buckle 120 turns on a limit switch 201 illustrated in FIG. 11. Then, this ON signal of the limit switch 201 is compared with a detecting signal detected based on the movement of the plunger 104 to confirm the presence or absence of the tubes 7, 8.

If an ON signal of the limit switch 201 is input in a condition where the tubes 7, 8 are not set, the controller confirms a tube setting failure or the absence of tubes and indicates thereof by a sound or the like to the user. On the other hand, if an ON signal of the limit switch 201 is input with the tubes 7, 8 being set, the controller waits for a following signal representative of start of tube connection.

After the driving of the tube connecting apparatus is started, it is necessary to prevent the movable clamps 12, 82 from being erroneously opened. In case the movable clamps 12, 82 are erroneously opened, this would release clamping of the tubes 7, 8, and thus the tubes cannot be held anymore.

Thus, a solenoid 202 shown in FIG. 10 is energized in response to the ON signal of the limit switch 201, causing a plunger 203 to be moved upward. With this arrangement, the plunger 203 is moved up into orbit in an opening direction of the pressing protruding piece 124 located as shown in FIG. 11 to prevent rotation of the buckle 120 itself, thereby preventing opening of the movable clamps 12, 82.

Next, when the movable clamps 12, 82 are closed into contact with the fixed clamps 11, 81, the positioning protrusions 21, 89 are inserted into the hollow movable clamps 12, 82 (see FIG. 9 and FIG. 11) to be fitted therein with no clearance in a lateral direction (lengthwise of the tubes), preventing lateral misalignment. Thus, the movable clamps 12, 82 can be closed in accurate positions with respect to the fixed clamps 11, 81. It is noted that the hollow portions of the movable clamps 12, 82 into which the positioning protrusions 21, 89 are inserted correspond to positioning holes of the invention.

At this time, in the first tube holder 1 side, the positioning protrusion 21 inserted in the movable clamp 12 comes into contact with the flat spring 71, then pushes the spring 71 to retract as shown in FIG. 9. Thus, the flat spring 71 is warped and deformed by the pressing force of the positioning protrusion 21, and the engaging piece 72 is accordingly retracted to be detached from the locking groove 37b of the clamp rotor 30.

When the user then locks the buckle 125, its pressing protruding piece 128 comes into contact with the end of the crank plate 66 projecting out from the window portion 26 of the fixed clamp 11 (represented by the broken line in FIG. 9) to push inward the crank plate 66. Consequently, the crank plate 66 is oscillated about the pin 68b being a fulcrum with the other end of the plate 66 pushing the hook portion 65q of the slide plate 65. Accordingly, the slide plate 65 is slid against the urging force of the spring 67, retracting the engaging portion 65p to be detached from the locking groove 37a of the clamp rotor 30. As a result, the clamp rotor 30 (rotor pieces 31, 32) is enabled to rotate.

After completion of proper clamping of the tubes 7, 8 as described above, the tube connecting apparatus enters a standby mode of waiting for a signal from a start switch. In this state, when the user then depresses the start switch, each of the mechanisms of the apparatus is driven to perform cutting and connecting of the tubes. At this time, the wafer 6 is first exchanged.

Such an exchange is performed because one wafer 6 is used for each tube connecting operation and the wafer 6 used in the last operation remains left within the wafer holder 40 (see FIG. 1). Therefore, upon depression of the start switch, exchange of the wafer 6 is performed through the following actions (see FIG. 1 and FIG. 2).

Upon depression of the start switch by the user, the stepping motor 5 is driven and the rotational force thereof is transmitted to the male screw 172 constituting the ball screw by means of the driving gear 174 and the transmission gear 173. The male screw 172 is accordingly rotated, causing the female screw block 163 of the female screw engaging with the male screw 172 to move in the axial direction. At this time, the female screw block 163, formed integrally with the slider 162 supported on the guide rod 171, is prevented from rotating by the slider 162. The driving of the stepping motor 5, therefore, also allows the slider 162 to slide on the guide rod 171 in the axial direction in association with the movement of the block 163, thus moving the transferring top 161 and the operating rod 195 in the same direction.

The stepped claw portion 161a of the tip end of the transfer top 161 is moved in the direction indicated by an arrow X in FIG. 2 and catches the rear end of a new wafer 6 to push the wafer 6 forward. At this time, a single wafer 6 is drawn out from the wafer cassette 160. The wafer 6 pushed by the transfer top 161 is transferred in the direction X while keeping its upright state and is slid into the groove in the wafer holder 140.

The movement of the slider 162 in the direction X not only makes the transfer top 161 transfer the wafer 6 but also makes the operating rod 195 perform opening and closing operations of the wafer holder 140. Specifically, when the slider 162 is moved in the direction X, the operating rod 195 which is pin-supported by the tip end of the supporting arm 168 is similarly slid in the direction X on the rail 192. At this time, the operating rod 195 can be moved straight forward without falling off from the rail 192 since the guide groove 195a is fitted on the guide pin 193 fixed on the rail 192. A tip end of the operating rod 195 slid on the rail 192 in the direction X is inserted between the fixed clamp 81 of the second tube holder 2 and the wafer holder 140. Since the operating rod 195 is synchronously moved with the movement of the transfer top 161 via the slider 162, opening and closing of the wafer holder 140 by the operating rod 195 is performed in timed relation to insertion of the wafer 6 into the wafer holder 140.

In the path of the operating rod 195, which is moved into between the fixed clamp 81 and the wafer holder 140 in synchronization with the transfer of the wafer 6 in the direction X, disposed is the linear projection 145s of the opening/closing plate 145 of the wafer holder 140 (see FIG. 15), as mentioned above. Accordingly, when the tip end of the rod 195 moving forward comes into contact with an end portion of the linear projection 145s. However, both the tip end of the operating rod 195 and the end portion of the linear projection 145s are tapered to prevent the operating rod 195 from abutting against the end portion of the linear projection 145s. Thus, the rod 195 can be smoothly moved forward along the linear projection 145s while laterally pressing the opening/closing plate 145. In association therewith, a lower portion of the plate 145 including the linear projection 145s is pushed toward the fixing plate 143 side, while an upper portion of the opening/closing plate 145 including the pressing piece 145b is separated from the fixed plate 143. The opening/closing plate 145 is turned in this manner into an open state. Thereafter, the lower portion of the plate 145 remains pushed by the operating rod 195 sliding forward along the linear projection 145s, maintaining the open state of the plate 145.

Then, the wafer 6 is transferred into the wafer holder 140 in timed relation to the opening movement of the opening/closing plate 145. This opening/closing plate 145 is held in the open state until the wafer 6 is completely placed in a specified position.

The position of the wafer 6 loaded in the wafer holder 140 is adjusted by a stop position of the transfer top 161. In conjunction with the transfer top 161, as shown in FIG. 2, the marker 167 is moved and then detected by the transfer-detecting sensor 186. Specifically, the position of the transfer top 161 at which the marker 167, moved together with the top 161, is detected by the sensor 186 is the specified position of the wafer 6 within the wafer holder 140.

Thus, when the marker 167 is moved in the direction X together with the transfer top 161 and is detected by the detecting sensor 186, a detection signal from the sensor 186 is transmitted to the controller. Upon receipt of the detection signal, the controller causes the stepping motor 5 to rotate in a reverse direction.

The reverse rotation of the motor 5 causes reverse rotation of the male screw 172 to move the female screw block 163 and the slider 162 in the direction opposite to the direction X. The transfer top 161 is then retracted, while only the wafer 6 is left in the wafer holder 140.

When the transfer top 161 is returned to the position as illustrated in FIG. 2, the standby-detecting sensor 185 detects the marker 166 and transmits a signal indicative thereof to the controller to cause the stepping motor 5 to stop rotation.

As above, the moving positions of the slider 162 and others are detected by the standby-detecting sensor 185 and the transfer-detecting sensor 186 and controlled based on the detection results of the sensors. The specified position of the wafer 6 or the standby positions of the slider 162 and others may be finely adjusted by changing inclinations of the markers 166, 167 with respect to the sensors 185, 186 fixed to the control substrate 183.

Returning to the time of loading of the wafer 6 into the wafer holder 140 (see FIGS. 14 and 15), the wafer 6, pushed by the transfer top 161, is slid into the groove formed between the base plate 141 and the fixed plate 143. In positions in the path of the wafer 6 are arranged the positioning flat springs 147a, 147b, and 147c pressed against the fixing plate 143 by the urging force. Thus, the wafer 6 is moved forward while pressed into contact with the fixing plate 143 by the springs 147a–147c to the specified position mentioned above.

On the other hand, the wafer 6 used in the last operation remains loaded in the wafer holder 140. This older wafer 6 is also pressed against the fixing plate 143 by the springs 147a, 147b, and 147c. Therefore, end faces of wafers 6, 6 (i.e., the rear end of the older one and the front end of the new one) surely abut against each other in spite of their very thin thicknesses of several hundreds of μm, so that the older wafer 6 is pushed out from the wafer holder 140 by the new wafer 6. Thus, exchange of the wafers 6 can be reliably performed.

When the wafer 6 is transferred to the specified position in the wafer holder 140, the rear end of the wafer 6 having passed the retraction preventing flat spring 148, the tip end of the flat spring 148 is pressed into contact with the fixed plate 143, so that the turned end 148a of the tip end interrupts the retracting path of the wafer 6. Accordingly, in cases where the user attempts to take the older wafer 6 which has been pushed out from the holder 140, even if the newly loaded wafer 6 is erroneously pushed by the older wafer 6, the new wafer 6 is prevented from moving back by the turned end 148a of the spring 148 and thus can be held in the specified position.

When the operating rod 195 is retracted together with the slider 162 in the above-described manner, the opening/closing plate 145 is released from the pressing by the rod 195 and turned back from the open state to the closed state by the urging members (not shown). Then, the electrodes 146a, 146b disposed on the opening/closing plate 145 come into contact with the terminal of the resistor of the wafer 6, energizing the resistor to raise the temperature of the wafer 6, for example, up to approximately 300° C. in the present embodiment.

When the temperature of the wafer 6 is sufficiently raised, cutting of the tubes 7, 8 may be performed. This cutting operation is performed by oscillating (rotating) the wafer holder 140 to move up the wafer 6 in an orthogonal direction to the tubes 7, 8 clamped by the first tube holder 1 and the second tube holder 2. Such oscillation of the wafer holder 140 is caused by transmitting rotation of the stepping motor 4 (see FIG. 2) to the driving cam 92 (see FIG. 10).

Specifically, when the stepping motor 4 is actuated, its rotational output is transmitted through the driving gear 96 fixed to the motor shaft 4a to the reduction gear 95, causing the driving cam 92 integrally formed with the reduction gear 95 to rotate. As the driving cam 92 is rotated, a height of the peak portion of the cutting cam 94 on which the roller bearing 155 of the wafer holder 140 is put is varied. Accordingly, the wafer holder 140 is oscillated up and down through the roller bearing 155 raised and lowered in relation to the rotation of the cam 92.

As shown in FIG. 2, the end surface of the oscillation tube 142 of the wafer holder 140 is pressed against the fixed clamp 81 by the spring 153. Therefore, the end surface 151A of the attaching block 151 and the end surface 152A of the sliding tube 152, both of the end surfaces 151A and 152A being flush with the end surface 142A of the oscillation tube 142, make contact with the lateral wall 85 (a reference surface) of the fixed clamp 81.

By rotation of the driving cam 92, as mentioned above, upward oscillating (rotating) movement of the wafer holder 140 about the oscillation tube 142 is performed. At this time, the end surface 142A is rotated about the guide rod 91 in contact with the lateral wall 85 of the fixed clamp 81 (see FIG. 10), while the end surfaces 151A and 152A are slid along the lateral wall 85. Thus, the wafer holder 140 can be oscillated up along the lateral wall 85 without deflecting or wobbling, allowing the wafer 6 to move in an orthogonal direction with respect to the tubes 7, 8. It should be noted that slide tapes (not shown) for restricting sliding resistance are adhered to sliding area of the lateral wall 85 (a reference surface) corresponding to the end surfaces 142A, 151A, and 152A, thereby enabling smooth oscillating movements of the wafer holder 140.

The heated wafer 6 loaded in the wafer holder 140 when moved up as above comes into contact from below with the tubes 7, 8 clamped by the first and second tube holders 1 and 2, thus melting the portions of the tubes contacting with the wafer 6 to cut the tubes.

Figure 16:
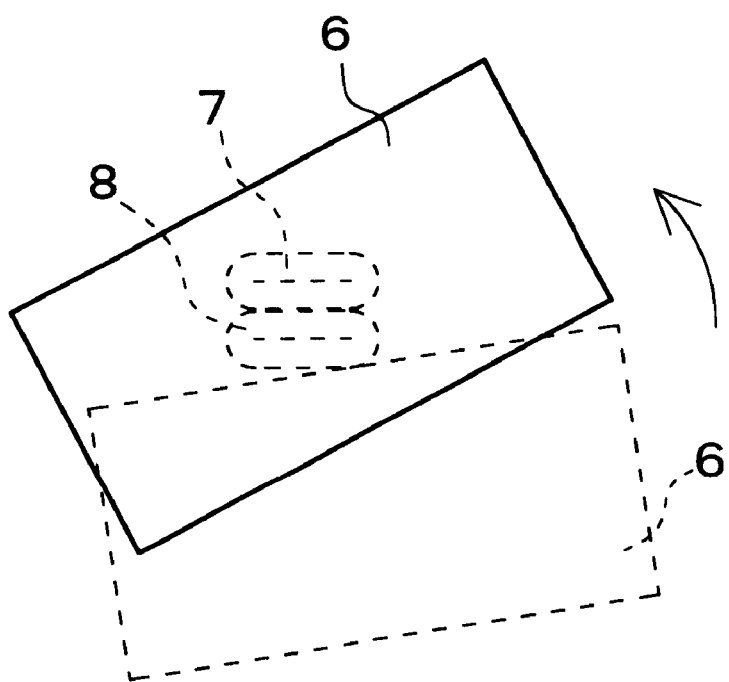
FIG. 16 is an explanatory view of showing a position of the wafer which cuts tubes.

FIG. 16 is a view showing positions of the wafer 6 in cutting the tubes 7, 8.

A cutting side (upper side) of the heated wafer 6 is brought into contact with the tubes 7, 8 from below (as indicated by a dotted line in FIG. 16) and then is slid obliquely by the oscillation wafer holder 140 to accordingly cut the tubes 7, 8 (as indicated by a solid line in FIG. 16). Accordingly, the contact portion of the cutting edge of the wafer 6 with the tubes 7, 8 is gradually shifted in the course of cutting, and the wafer 6 can retain an amount of heat in the contact portion thereby to melt and cut the tubes.

The retaining of the heat amount of the wafer 6 is required for the following reason. The cut end faces of the tubes 7, 8 need to be sufficiently melted to be welded after cutting. On the other hand, the wafer 6 will lose heat to the tubes 7, 8 during melting to cut them. The wafer 6 in itself is thin and has substantially no heat storage ability. When the wafer 6 cuts the tubes by using only one portion of the cutting edge, the temperature of this portion is remarkably decreased, disabling the wafer 6 in contact with the cut end faces to sufficiently melt them. As mentioned above, the obliquely sliding of the cutting edge of the wafer 6 with respect to the tubes 7, 8 can gradually shift the cutting portions so that the temperature thereof may be kept above a constant temperature sufficient to melt the cut end faces of the tubes. Thus the cut end faces of the tubes can be sufficiently melted for connection.

The cutting and welding of the tubes 7, 8 by the wafer 6 is performed at the closed portions of the tubes 7, 8 squeezed by the first tube holder 1 and the second tube holder 2 (see FIG. 13).

When the movable clamps 12, 82 are set on the fixed clamps 11, 81, the tubes 7, 8 held in the tube guide 40, 100 are clamped as shown in FIG. 1 by means of the closing portions 33a, 33b of the clamp rotor 30 (see FIG. 3) in the first tube holder 1 and by means of the holding groove 98 of the fixed clamp body 83 (see FIG. 10) as well as the closing portion 114 of the movable clamp body 110 (see FIG. 12) in the second tube holder 2. Therefore, the tubes 7, 8 appearing between the first and second tube holders 1 and 2 are flattened with the interiors tightly closed. The flattened portions in question are to be cut by the wafer 6 and then to be welded.

Hence, the wafer 6 is obliquely moved up as above by the oscillating movement of the wafer holder 140 to cut the tubes 7, 8 as shown in FIG. 16. The tubes 7, 8 have been clamped and squeezed in advance such that liquid in the tubes is pushed away from the cutting portions at clamping, preventing liquid leakage when the tubes 7, 8 are cut.

At the time of cutting the tubes, the cut ends of the tubes 7, 8 are hot in a condition of melted or softened resin, and therefore are in contact in an airtight manner with the wafer 6. Therefore, the interiors of the tubes 7, 8 are prevented from being exposed to the atmosphere and maintained in an aseptic condition until the connecting of the cut ends of the tubes is performed subsequently to the cutting.

Next, of the tubes 7, 8 which have been cut apart by the wafer 6, the cut portions clamped by the first tube holder 1 are inverted by rotation of the clamp rotor 30 in the following manner. The driving of the stepping motor 4 is stopped when the wafer 6 is sufficiently moved up and subsequently the stepping motor 3 (see FIG. 2) is driven to rotate the clamp rotor 30. Specifically, as shown in FIG. 9, the rotation of the stepping motor 3 is transmitted from the driving gear 61 attached to the motor shaft 3a to the rotor gear 36 of the clamp rotor 30 through the access gear 62 and the drive gear 63. Thus, the clamp rotor 30 is rotated as a single rotor made of the rotor pieces 31, 32 as shown in FIG. 9.

Figure 19:
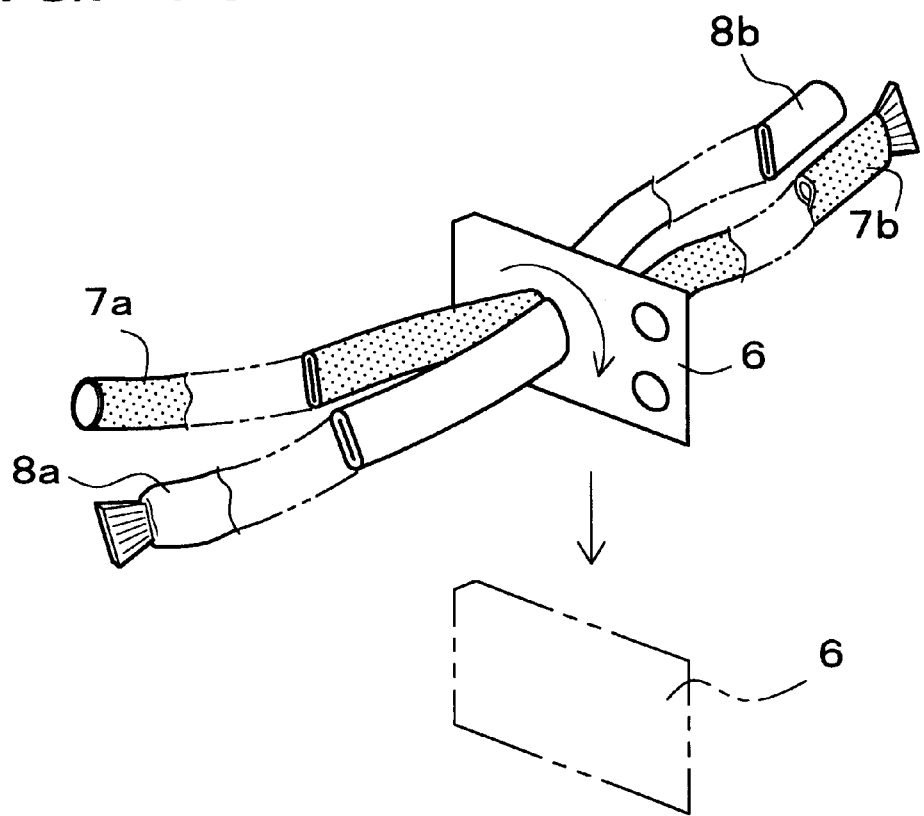
FIG. 19 is an explanatory view of showing tubes in cutting and inversion.

The stepping motor 3 is operated until the clamp rotor 30 is rotated 180° such that the rotor pieces 31, 32 change positions in relation to the fixed clamp 11 and the movable clamp 12. Therefore, positions of the two cut tubes 7a, 8a clamped vertically one on top of the other are inverted, similarly to the case as shown in FIG. 19.

At this time, the clamp rotor 30, being rotationally supported by means of rollers 20, 20, 20, 55, 55, 55 arranged at circumferentially equally spaced intervals, can rotate accurately about a virtual rotational axis.

Also, the cut tubes 7a, 8a have been clamped such that their cut end faces are in contact with the wafer 6 and are positioned one over the other with respect to the rotational axis of the rotor 30. By the 180° rotation of the rotor 30, changing positions of the rotor pieces 31 and 32, accordingly, the cut end faces of the tubes 7a, 8a can be rotated about the rotational axis to be accurately placed respectively in the positions of the tubes 8a, 7a before inverting.

Figure 17A:
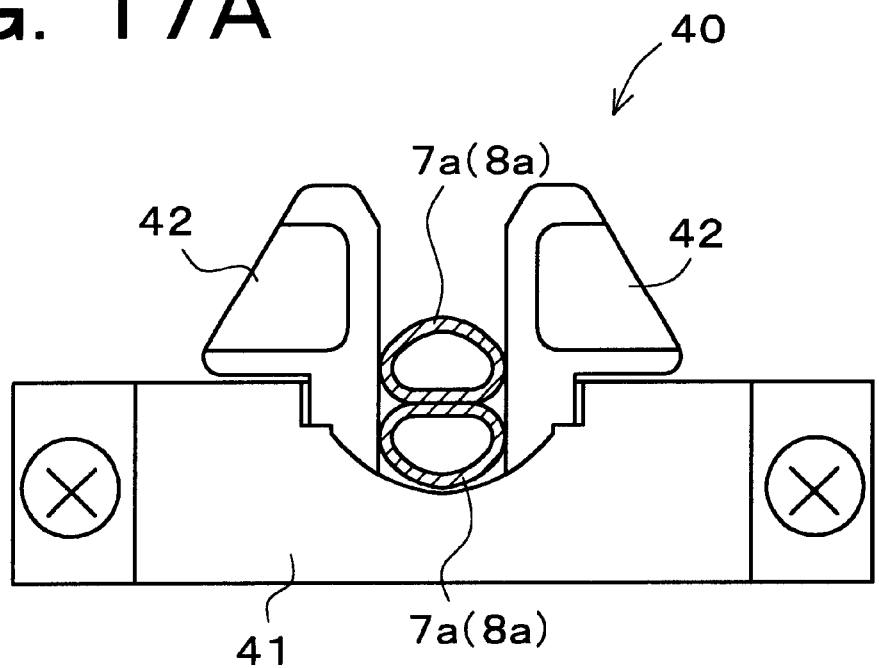
FIGS. 17A and 17B are side views of the tube guide in the embodiment, showing a state of clamping tubes.
Figure 17B:
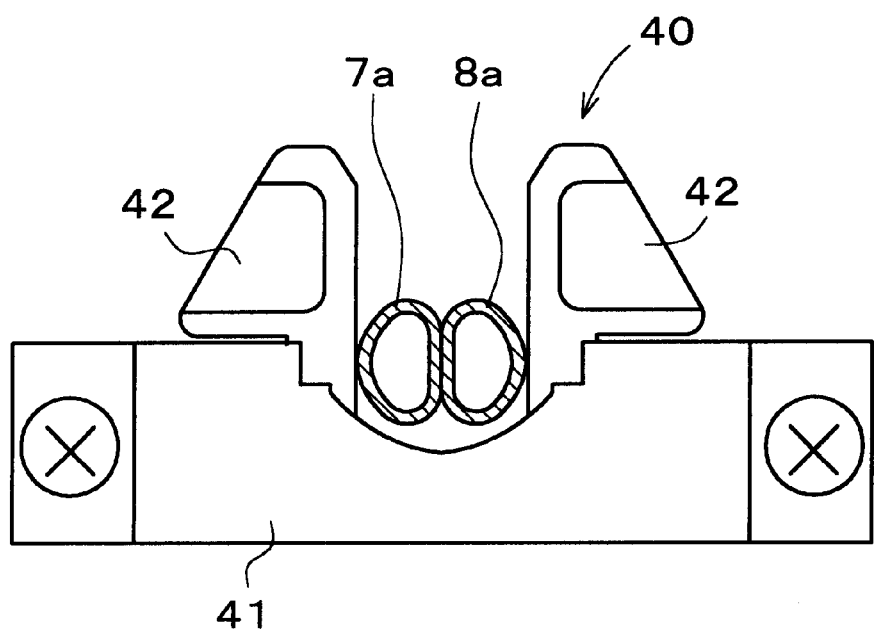
Figure 18:
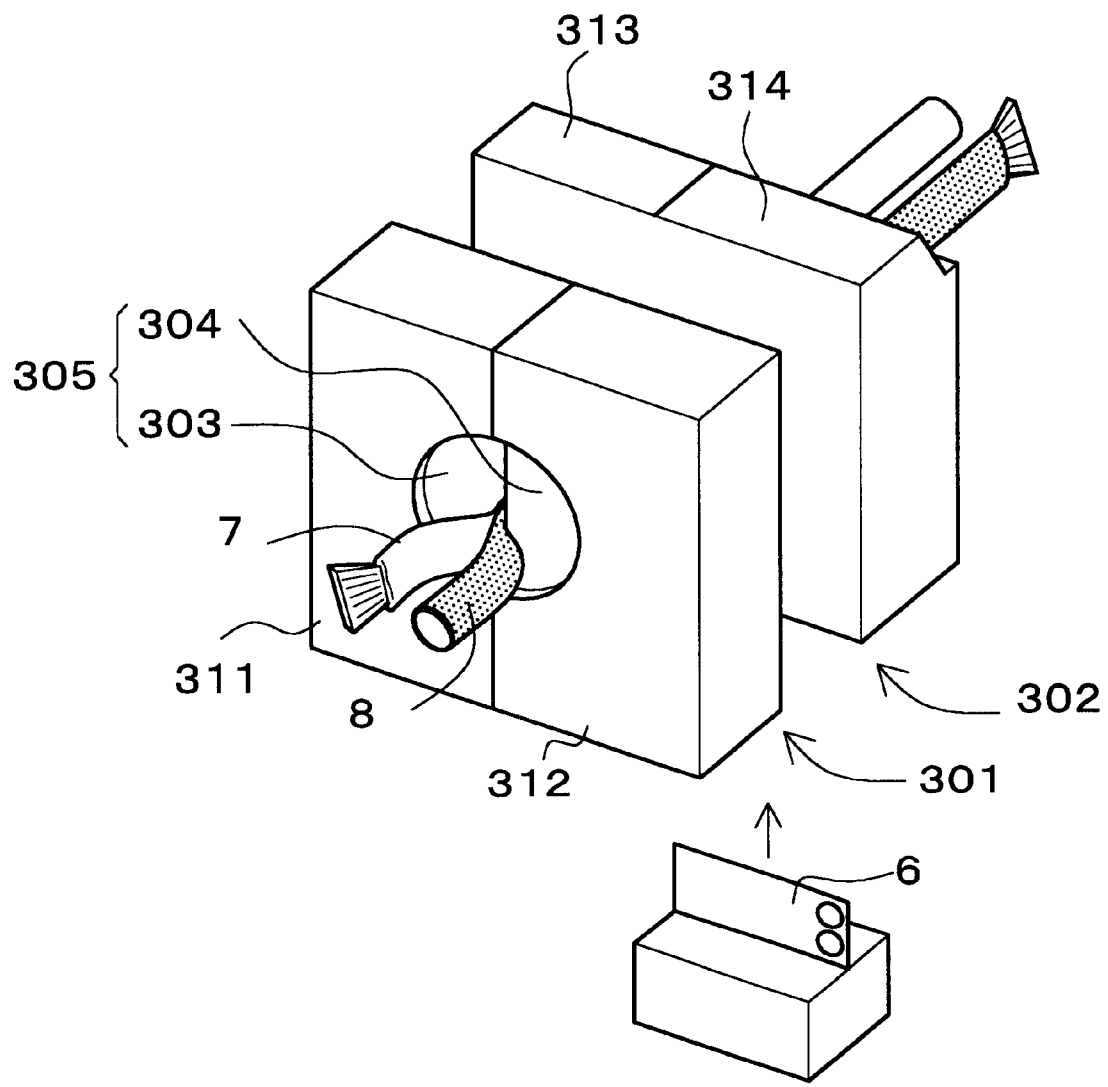
FIG. 18 is a perspective view of a tube clamping part of a conventional tube connecting apparatus.

The tube guide 40 during inversion of the tubes 7a, 8a will be explained below. FIGS. 17A and 17B are side views of the tube guide 40 in the present embodiment, showing the state where the tube guide 40 clamps the tubes 7, 8.

Before rotation of the clamp rotor 30, the cut tubes 7a, 8a are held vertically one on top of the other and are pinched between the guide claws 42, 42 from both sides as shown in FIG. 17A. The cut tubes 7a, 8a are then rotated in accordance with the clamp rotor 30. By a 90° rotation of the clamp rotor 30, the tubes 7a, 8a will be disposed alongside each other as shown in FIG. 17B. Subsequently, when the rotor 30 is further rotated 90° the tubes 7a, 8a are inverted from the positions before its 180° rotation to the positions (8a, 7a) as indicated in parentheses in FIG. 17A. In association with rotation of the tubes 7a, 8a, the lateral dimensions of the two tubes 7a, 8a become larger as shown in FIG. 17B. At this time, the springs 43, 43 (see FIG. 7) of the tube guide 40 will be compressed in lateral directions by the tubes 7a, 8a, and the guide claws 42, 42 moved outwards, i.e., away from each other, to widen the distance between the claws 42, 42.

Accordingly, the tube guide 40 can function to reliably hold the tubes 7a, 8a regardless of how the tubes are therein arranged in parallel with each other (side-by-side or one on top of the other) by adjusting the guide claws 42, 42 into contact with the tubes in correspondence with the rotation of the tubes, specifically, by moving the guide claws 42, 42 outwards (away from each other) as the tubes are rotated, thereby enabling a smooth inverting operation.

Figure 20:
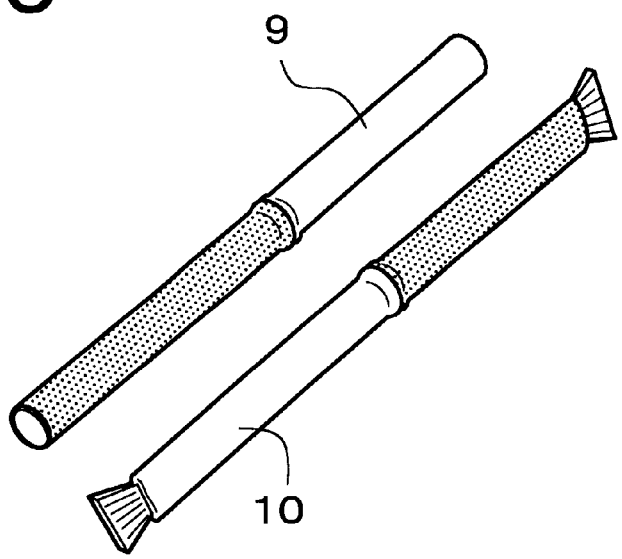
FIG. 20 is a perspective view of resultant tubes after connection between different tubes.
Figure 21:
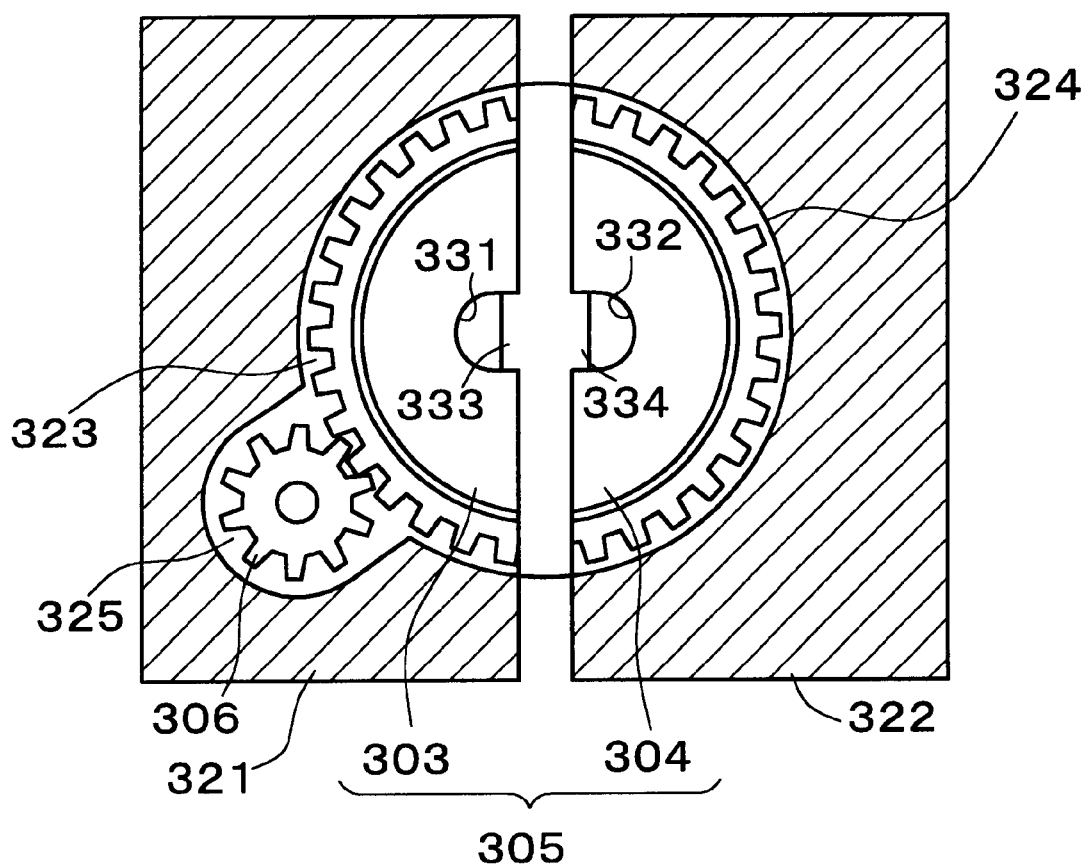
FIG. 21 is a sectional view of an inverting mechanism of the conventional tube connecting apparatus.

The cut ends of the tubes 7a, 8a, which have been inverted, are disposed to face the cut ends of the tubes 8b, 7b clamped in the second tube holder 2 (see FIG. 19) through the wafer 6 like the state immediately after cutting. Thereafter, when the wafer 6 is moved down and both cut ends of the different tubes are brought into contact with each other in the axial direction, the cut end faces of the cut tubes 7a, 8a are welded to those of the cut tubes 8b, 7b respectively to form two tubes 9, 10 (FIG. 20).

Specifically, the stepping motor 3 that has inverted the clamp rotor 30 is first stopped and subsequently the stepping motor 4 is actuated again. Thus, the driving cam 92 (see FIG. 10) is rotated to change the height of the peak portion of the cutting cam 94 into low, on which the roller bearing 155 (see FIG. 15) is put, and the wafer holder 140 is moved down in association therewith. In this manner, the wafer 6 is simultaneously moved down to be withdrawn from between the tubes 7a, 8a and the tubes 8b, 7b. At this time, the wafer 6 is hooked by the stop portions 143a, 143b, so that the wafer 6 is prevented from coming off the wafer holder 140.

The driving cam 92 for allowing the wafer holder 140 to move down is integrally constructed of the cutting cam 94 and the slide cam 93 for moving the first tube holder 1. Accordingly, simultaneously with the moving-down (oscillating-down) of the wafer holder 140 to withdraw the wafer 6 from between the cut tubes 7a, 8a and the cut tubes 8b, 7b, the sliding of the first tube holder I toward the second tube holder 2 side is uniquely performed. Thus, the cut end faces of the tubes 7a and 8a are pressed against the cut end faces of the different tubes 8b and 7b in the axial direction at a predetermined timing.

The first tube holder 1 is always urged by the spring 131 (see FIG. 1) with the roller bearing 25 of the pressing arm 24 (see FIG. 6) brought into contact with the slide cam 93 of the driving cam 92 (see FIG. 10). Thus, while the wafer holder 140 is moved up by rotation of the driving cam 92, the roller bearing 25 is made to roll on the flat surface portion of the slide cam 93, and the distance between the first tube holder 1 and the second tube holder 2 is maintained constant. Timed to the withdrawal of the wafer 6 from the tubes 7, 8, the slide cam 93 being rotated, the roller bearing 25 comes into contact with the sloped slide cam surface 93a of the slide cam 93, rolling thereon, at a timing of the withdrawal of the wafer 6 from between the cut ends of the tubes 7, 8.

The first tube holder 1 is thus pushed toward the second tube holder 2 by the urging force of the spring 131 with the slide tube 22 being slid on the guide rod 91 and the guide roller 23 being rotated in the guide block 29 for movement of the holder 1 with respect to the holder 2 in parallel relation.

Thus, the first tube holder 1 is moved closer to the second tube holder 2 side by the distance corresponding to a difference in height between the flat surface of the slide cam 93 and the slide cam surface 93a, though it is a very short distance. This is for pressing to connect the cut end faces of the tubes by moving the cut tubes 7a, 8a for a cutting width (approximately thickness of the wafer 6).

The cut end faces of the tubes 7, 8 will be welded by pressing the cut end faces to those of the different tubes, thus forming two tubes 9, 10 which have been mutually translocated as shown in FIG. 20.

It should be noted that the pin 129 of the buckle 125 has been inserted into the inserting groove 122 of the buckle 120, and the buckle 125 of the first tube holder 1 is attached to the buckle 120 of the second tube holder 2 with play. The buckle 125 of the first tube holder 1 is thus movable along the groove 122 with respect to the buckle 120 of the second tube holder 2. Thus, the connection between the buckle 125 of the first tube holder 1 and the buckle 120 of the second tube holder 2 will not interfere with the slight movement of the first tube holder 1 towards the second tube holder 2 in a parallel arrangement.

Completion of the moving-down of the wafer holder 140 is detected by a limit switch 205 (see FIG. 10) attached to the fixed clamp 81. Upon this detection, the plunger 203 of the solenoid 202 is moved down, thereby enabling detachment of the buckles 120, 125 from the fixed clamps 11, 81.

Then, the user may detach the buckles 120, 125 and open the movable clamps 12, 82 for taking out the tubes 9, 10. In the above described manner, the tube connecting operation is completed.

After that, the first tube holder 1 moved to the second tube holder 2 side stays in this position until the next tube connecting operation is performed.

When a power switch of the apparatus is turned on for the next tube connecting operation, the plunger 104 in the fixed clamp 81 of the second tube holder 2 (see FIG. 11) detects the absence of tube. Based on this detection result, the stepping motor 4 is actuated so that the rotation of the driving cam 92 is adjusted to move the first tube holder 1 away from the second tube holder 2.

It is to be noted that when the buckles 120, 125 are detached and the movable clamps 12, 82 are opened, the rotor pieces 31, 32 are locked again (see FIG. 9).

This locking is performed in the following manner. At first, when the user first detaches the buckle 125, the pressing protruding piece 128 thereof is rotated to release the crank plate 66, removing the restriction on the slide plate 65 through the crank plate 66, thus enabling sliding of the slide plate 65. The slide plate 65 is slid toward the clamp rotor 30 by the urging force of the spring 67 such that the engaging portion 65p is inserted into the locking groove 37a.

On the other hand, when the movable clamp 12 is opened as shown in FIG. 1, the positioning protrusion 21 inserted in the movable clamp 12 is relatively detached. Accordingly, the flat spring 71 becomes free and the engaging piece 72 is pushed by the urging force of the spring 71 into the locking groove 37b of the clamp rotor 30.

In the above manner, upon opening of the movable clamp 12, the rotor pieces 31, 32 are locked in positions at which the tubes have been inverted in the above-mentioned operation.

In the tube connecting apparatus in the present embodiment, due to the provision of the locking mechanism in the fixed and second clamps 11 and 12 mounting therein the rotor pieces 31 and 32, respectively, the rotor pieces 31 and 32 are prevented from being displaced in the fixed clamp 11 and the movable clamp 12 in case the user should push the rotor pieces 31, 32 during opening of the movable clamp 12 as illustrated in FIG. 1. Consequently, when the movable clamp 12 is set on the fixed clamp 11 again as illustrated in FIG. 9, the rotor pieces 31, 32 can be positioned vertically symmetrically, which prevents the clamp rotor 30 from being displaced in the rotational direction before driving.

Inversion of the tubes can also be reliably performed by the rotation of the clamp rotor 30 to thereby ensure reliable connection of the cut end faces of the different tubes.

Further, the locking mechanism provided in the movable clamp 12 is arranged such that the engaging piece 72 for locking the rotor pieces 31, 32 is retracted from or inserted in the locking groove 37b by the positioning protrusion 21 which comes in or out of the movable clamp 12 in association with opening/closing of the movable clamp 12. The rotor pieces 31, 32 can be surely locked in case the user touches them in the open state as illustrated in FIG. 1.

The locking mechanism provided in the fixed clamp 11 is arranged such that the engaging portion 65p of the slide plate 65 is inserted into and retracted from the locking groove 37a in association with locking/releasing operations of the buckle 125. Thus, similarly to above, the rotor pieces 31, 32 can be reliably locked in case the user touches them in the open state as illustrated in FIG. 1.

By cooperation of the engaging portion 65p and the engaging piece 72 with the locking grooves 37a, 37b of the rotor pieces 31, 32, the rotor pieces 31, 32 can be uniquely positioned to be symmetrical between before and after inversion of the clamp rotor 30 as illustrated in FIG. 9

Further, the locking grooves 37a, 37b are configured such that the opposite inner wall surfaces of two protruding walls constituting a groove are substantially parallel. In relation therewith, the engaging portion 65p and the engaging piece 72 which are inserted therein are formed in a square shape having peripheral faces corresponding to the inner wall surfaces.

According to the tube connecting apparatus of the present embodiment, when the movable clamps 12, 82 are set on the fixed clamps 11, 81, the positioning protrusions 21, 89 prevent displacement of the movable clamps 12, 82 in a lateral direction (which is perpendicular to a lengthwise direction of the movable clamps 12, 82) with respect to the fixed clamps 11, 81, realizing alignment therebetween.

In this manner, the rotor pieces 31, 32, prevented from being displaced can constitute an accurate clamp rotor 30 when the movable clamps are set on the fixed clamps. This can prevent connection failure of the tubes. The tubes 7, 8 are reliably clamped with their interiors closed by the closing portions 33b, 33b of the clamp rotor 30 in the first tube holder 1 (see FIG. 3) and by the holding groove 98 of the fixed clamp body 83 (see FIG. 10) and the closing portion 114 of the movable clamp body 110 (see FIG. 12) in the second tube holder 2. This makes it possible to prevent leakage of liquid from the tubes when cut.

According to the tube connecting apparatus of the present embodiment, the user can accurately dispose the tubes 7, 8 by using the tube guides 40, 100. More particularly, the distance between the guide claws 42, 42 of the tube guide 40 (see FIG. 7) and that of the guide claws 101, 101 of the tube guide 100 (see FIG. 11) can be adjusted to suit the outer diameters of the tubes 7, 8. The tubes 7, 8 may be accurately set such that their central axes are in parallel disposed one on top of the other.

The guide claws 101, 101 are formed with the protrusions 101a, 110a at inner sides of the tip end portions, preventing coming off of the tubes.

According to the tube connecting apparatus of the present embodiment, due to the provision of the plunger 104 in the fixed clamp 81 of the second tube holder 2 for detecting that the tubes 7, 8 have been held, it is possible to stop tube connecting operations in a condition where the tubes 7, 8 are not held, thereby avoiding connection errors likely to be caused by clamping errors of the tubes.

At this time, since the bottom surface of the holding groove 103 from which the plunger 104 is protruded is formed flat, the area of contact surfaces of the tubes 7, 8 with respect to this bottom surface is small. The elastic force of the tubes 7, 8 is therefore strongly exerted on the contact surfaces. Thus, the plunger 104 protruding to the contact surfaces may be reliably pressed down by the elastic force of the tubes 7, 8.

Furthermore, the tubes 7, 8 clamped by the clamp rotor 30 are symmetrically squeezed with respect to an intermediate point of respective central axes, while the tubes 7, 8 clamped by the holding groove 98 and the closing portion 114 are squeezed as to be pressed to the bottom surface of the holding groove 98 side. Accordingly, the elastic force of the tubes 7, 8 may strongly act on the bottom surface of the holding groove 98 side, ensuring pressing of the plunger 104 and making it possible to improve detecting accuracy of the sensor for tubes.

According to the tube connecting apparatus of the present embodiment, the tube guide 40 in the first tube holder 1 in which the clamp rotor 30 is rotated is configured such that the guide claws 42, 42 are slidable. Therefore, the guide claws 42, 42 can reliably hold therebetween the tubes 7a, 8a regardless of how the tubes are arranged in parallel with each other, namely, side-by-side or one on top of the other. Specifically, the guide claws 42, 42 can surely support the tubes when disposed one over the other, while mutually sliding outwards to thereby permit the tubes to be smoothly inverted.

According to the tube connecting apparatus of the present embodiment, the buckle 125, pivotally provided in the movable clamp 12 of the first tube holder 1, is attached with play to the buckle 120 pivotally provided in the movable clamp 82 of the second tube holder 2 (see FIG. 13). The pressing of the cut end faces of the tubes 7a, 8a to those of the tubes 8b, 7b can be ensured even when the movable clamp 12 of the first tube holder 1 and the movable clamp 82 of the second tube holder 2 are integrally connected through the buckles 120, 125. Thus, the movable clamps 12, 82 are no more required to be individually manipulated when moving the movable clamp 12, 82 with respect to the fixed clamps 11, 81. The movable clamps 12, 82 can be operated as a single unit due to the buckle 120, 125, making it possible to eliminate the need for individual manipulation of the movable clamps 12, 82, thus improving operability thereof.

In the tube connecting apparatus of the present embodiment, when the tubes 7, 8 are held in the first tube holder 1 and the second tube holder 2, the movement of the plunger 203 caused in correspondence of excitation and demagnetization of the solenoid 202 prevents release of the tubes 7, 8 from the first tube holder 1 and the second tube holder 2 under a predetermined condition of operation, or for a predetermined period of operation (in the above embodiment, this period indicates the period of from the locking of the buckle 120, 125 to the completion of moving-down of the wafer holder 140) of the apparatus after holding the tubes 7, 8. With this arrangement, the first tube holder 1 and the second tube holder 2 can be prevented from erroneously releasing the tubes 7, 8 until completion of the connection thereof. The cut end faces of the tubes 7a, 8a can be reliably connected to those of the different tubes 8b, 7b.

It is to be noted that the present invention is not limited to the above form of embodiment but may be variously modified without departing from the spirit thereof.

For instance, in the above embodiment, the locking grooves 37a and 37b, 37a and 37b are provided in the rotor pieces 31, 32, into which the engaging portion 65p and the engaging piece 72 are fitted for positioning the rotor pieces 31, 32 to lock them. The locking of the rotor pieces 31, 31 may be performed by alternatives to the engaging portion 65p and the engaging piece 72, which are merely inserted into rotor gears 36, 36 of the rotor pieces 31, 32.

Further, in the above embodiment, the locking mechanism in the fixing clamp 11 side is exemplarily configured in a sliding type whereas the locking mechanism in the movable clamp 12 side is configured using a flat spring. These may be exchanged or replaced by another types.

Furthermore, for instance, the positioning protrusions 21, 89 for accurately setting the movable clamps 12, 82 on the fixed clamps 11, 81 may be provided in the movable clamps 12, 82 side.

What is claimed is:

1. A tube connecting apparatus including:
   a first tube holder provided with a pair of holding members for holding a plurality of flexible tubes;
   a second tube holder provided with a pair of holding members for holding the plurality of flexible tubes,
      one or both of the first tube holder and the second tube holder including a pair of rotatable clamping members for holding the tubes, the clamping members including separable pieces disposed in rotational symmetry;
   cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and
   rotation preventing means for preventing rotation of the clamping members being in predetermined positions in the respective holding members while the pair of clamping members are in a state of not holding the plurality of flexible tubes.

2. The tube connecting apparatus according to claim 1, wherein the rotation preventing means is constructed of an engaging groove formed in the clamping member and a protrusion provided in a resilient member having an urging force toward the clamping member, the protrusion being insertable into the groove of the clamping member by the urging force of the resilient member, and the protrusion is retracted from the groove of the clamping member against the urging force of the resilient member by a pressing member that presses the resilient member away from the clamping member when the pair of clamping members hold the tubes.

3. The tube connecting apparatus according to claim 2, wherein the resilient member is a flat spring and is integrally formed with the protrusion insertable into the groove of the clamping member.

4. The tube connecting apparatus according to claim 2, wherein the groove of the clamping member is formed in the clamping member in a correspondent position with the protrusion.

5. The tube connecting apparatus according to claim 1, wherein the rotation preventing means is constructed of an engaging groove formed in the clamping member, an engaging slider formed with an engaging portion insertable into the groove of the clamping member, and a linkage mechanism for sliding the engaging slider forward and backward in synchronization with the pair of holding members operated to hold and release the tubes.

6. The tube connecting apparatus according to claim 5, wherein the linkage mechanism of the rotation preventing means includes a lever axially supported so as to be able to oscillate, the lever being oscillated by an external force applied thereto when the pair of holding members hold the tubes, thereby retracting the engaging slider urged to the clamping member against the urging force.

7. The tube connecting apparatus according to claim 5, wherein the groove of the clamping member is formed in the clamping member in a correspondent position with the engaging portion.

8. A tube connecting apparatus including:
  a first tube holder provided with a pair of holding members for holding a plurality of flexible tubes;
  a second tube holder provided with a pair of holding members for holding the plurality of flexible tubes,
    one or both of the first tube holder and the second tube holder including a pair of rotatable clamping members for holding the tubes, the clamping members including separable pieces disposed in rotational symmetry;
  cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes;
  wherein at least either one of the holding members of at least either one of the first tube holder and the second tube holder is provided with a positioning hole and the other one with a positioning protrusion engageable with the positioning hole, and positioning of the pair of holding members set together is performed by engaging the protrusion with the positioning hole.

9. A tube connecting apparatus including:
  a first tube holder provided with a pair of holding members for holding a plurality of flexible tubes;
  a second tube holder provided with a pair of holding members for holding the plurality of flexible tubes;
  cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and
  supporting means provided in at least either one of the first tube holder and the second tube holder for supporting the tubes to be arranged one over another, the supporting means being provided with a pair of supporting claws projecting for pinching the tubes therebetween, and the supporting claws each being formed with a protrusion for preventing the tubes from coming off.

10. A tube connecting apparatus including:
  a first tube holder provided with a pair of holding members for holding a plurality of flexile tubes;
  a second tube holder provided with a pair of holding members for holding the plurality of flexible tubes;
  cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and
  detecting means for detecting presence or absence of the tubes in at least one of the first tube holder and the second tube holder wherein the detecting means includes a plunger which protrudes in response to an urging force of an urging member and a sensor for detecting a position of the plunger, and
  the plunger is retracted by an elastic force of the held tubes against the urging force of the urging member and a position of the retracted plunger is detected by the sensor.

11. The tube connecting apparatus according to claim 10, wherein the plunger is provided in either or both of the tube holders and a surface from which the plunger projects is flat.

12. The tube connecting apparatus according to claim 10, wherein the pair of holding members is formed with a groove for holding the tubes, the groove being formed with closing members for flattening and closing the held tubes at one end thereof, the plunger is disposed within the groove, and a closing position at which the closing members close the tubes is closer to the plunger side than a center of the tubes.

13. A tube connecting apparatus including:
  a first tube holder provided with a pair of holding members for holding a plurality of flexible tubes;
  a second tube holder provided with a pair of holding members for holding the plurality of flexible tubes,
    one or both of the first tube holder and the second tube holder including a pair of rotatable clamping members for holding the tubes, the clamping members including separable pieces disposed in rotational symmetry;
  cutting and connecting means for heating and melting the plurality of flexible tubes held in the first tube holder and the second tube holder to cut the tubes by a heated cutting plate which is moved between the first tube holder and the second tube holder and to connect the tubes cut by the cutting plate by contacting cut end faces of the cut tubes held in the first tube holder with those of the cut tubes held in the second tube holder, the cut tubes to be connected being parts of originally different tubes; and
  supporting means for arranging the tubes one over another in an outside of at least either one of the first tube holder and the second tube holder;
  wherein the supporting means includes a pair of claws for pinching the tubes therebetween, the claws being urged in directions of moving toward each other by urging members and being movable away from each other in association with rotation of the tubes against the urging force of the urging members while the tubes are rotated as held by the clamping member.

* * * * *

UNITED STATES PATENT AND TRADEMARK OFFICE
CERTIFICATE OF CORRECTION

PATENT NO.     : 6,460,592 B1
DATED          : October 8, 2002
INVENTOR(S)    : Hiroaki Sano et al.

It is certified that error appears in the above-identified patent and that said Letters Patent is hereby corrected as shown below:

<u>Title page,</u>
Item [73], Assignee, change "Tervino Kabushiki Kaisha" to -- Terumo Kabushiki Kaisha --.

Signed and Sealed this

Fourth Day of February, 2003

JAMES E. ROGAN
*Director of the United States Patent and Trademark Office*